United States Patent [19]

Chandrasegaran

[11] Patent Number: 5,792,640

[45] Date of Patent: Aug. 11, 1998

[54] GENERAL METHOD TO CLONE HYBRID RESTRICTION ENDONUCLEASES USING LIG GENE

[75] Inventor: Srinivasan Chandrasegaran, Baltimore, Md.

[73] Assignee: The Johns Hopkins University, Baltimore, Md.

[21] Appl. No.: 575,361

[22] Filed: Dec. 24, 1995

Related U.S. Application Data

[63] Continuation-in-part of Ser. No. 346,293, Nov. 23, 1994, Pat. No. 5,487,994, which is a continuation-in-part of Ser. No. 126,564, Sep. 27, 1993, Pat. No. 5,436,150, which is a continuation-in-part of Ser. No. 17,493, Feb. 12, 1993, abandoned, which is a continuation-in-part of Ser. No. 862,831, Apr. 3, 1992, Pat. No. 5,356,802.

[51] Int. Cl.$^6$ .................................................. C12N 9/22
[52] U.S. Cl. ............................................ 435/199; 435/91.1
[58] Field of Search .................................. 435/199, 91.1

[56] References Cited

U.S. PATENT DOCUMENTS 5,200,333  4/1993  Wilson .............................. 435/172.3

OTHER PUBLICATIONS

Rima Youil et al., Screening for Mutations by Enzyme Mismatch Cleavage with T4 Endonuclease VII, Proc. Natl. Acad. Sci. USA, Jan. 1995, pp. 87–91, vol. 92.

Alla Lishanski et al., Mutation Detection by Mismatch Binding Protein, MutS, in Amplified DNA: Application to the Cystic Fibrosis Gene, Proc. Natl. Acad. Sci. USA, Mar. 1994, pp. 2674–2678, vol. 91.

Adrian Whitehouse et al., A Carboxy Terminal Domain of the hMSH–2 Gene Product is Sufficient for Binding Specific Mismatched Oligonucleotides, Biochemical and Biophysical Research Communications, 1996, vol. 225, 289–295, Article No. 1168.

Yang–Gyun Kim et al., Hybrid Restriction Enzymes: Zinc Finger Fusions to *FOK* I Cleavage Domain, Proc. Natl. Acad. Sci. USA, Feb. 1996, 1156–1160, vol. 93.

Yang–Gyun Kim et al., Chimeric Restriction Endonuclease, Proc. Natl. Acad. Sci. USA, Feb. 1994, pp. 883–887, vol. 91.

Lin Li et al., Functional Domains in *FOK* I Restriction Endonuclease, Proc. Natl. Acad. Sci. USA, May 1992, pp. 4275–4279, vol. 89.

Lin Li et al., C–terminal Deletion Mutants of the *FOK* I Restriction Endonuclease, Gene, 133 1993, pp. 79–84.

Lin Li et al., Alteration of the Cleavage Distance of *FOK* Restriction Endonuclease by Insertion Mutagenesis, Pro. Natl. Acad. Sci. USA, Apr. 1993, pp. 2764–2768, vol. 90.

Yang–Gyun Kim et al., Insertion and Deletion Mutants of *FOK* I Restriction Endonuclease, The Journal of Biological Chemistry, Dec. 16, 1994, pp. 31978–31982, vol. 269, No. 50.

Baohua Huang et al., Splase: A New Class IIS Zinc–Finger Restriction Endonuclease with Specificity for Sp1 Binding Sites, Journal of Protein Chemistry, 1996, pp. 481–489, vol. 15.

Yen Choo et al., In Vivo Repression by a Site–Specific DNA–Binding Protein Designed Against an Oncogenic Sequence, Nature, Dec. 15, 1994, pp. 642–645, vol. 372.

*Primary Examiner*—Charles L. Patterson, Jr.
*Attorney, Agent, or Firm*—Cushman Darby Cushman IP Group of Pillsbury Madison & Sutro LLP

[57] ABSTRACT

The present invention reveals methods for cloning hybrid restriction endonucleases and for enzymatically inactivating a target DNA. The method for cloning hybrid restriction endonucleases involves co-expression of a ligase. A first plasmid contains a gene encoding a DNA ligase. A second plasmid contains a gene encoding a hybrid restriction endonuclease and is compatible with the first plasmid. The method involves transfecting host cells with the first plasmid, so that DNA ligase is produced, followed by transfecting the cells with the second plasmid. The method for enzymatically inactivating a target DNA involves preparing a plasmid, phage, virus or any other delivery vehicle such as a liposome containing a gene encoding a nuclease, delivering the gene into cells, inducing the cells to produce the nuclease and enzymatically inactivating the target DNA.

32 Claims, 18 Drawing Sheets

FIG. IA
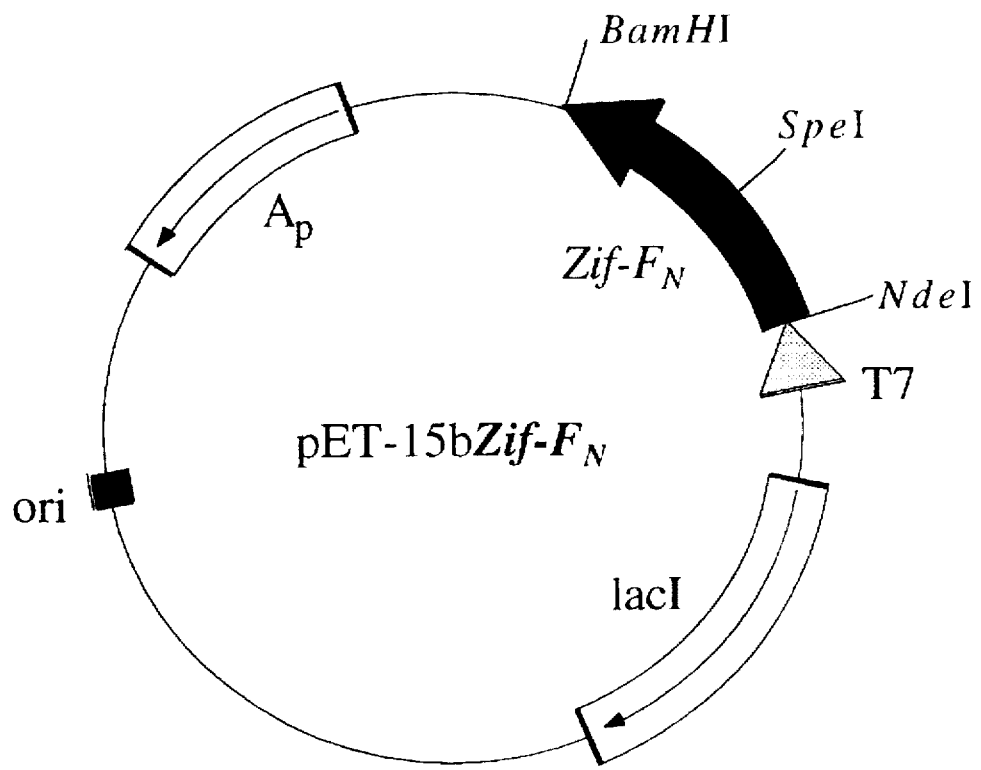
FIG. IB
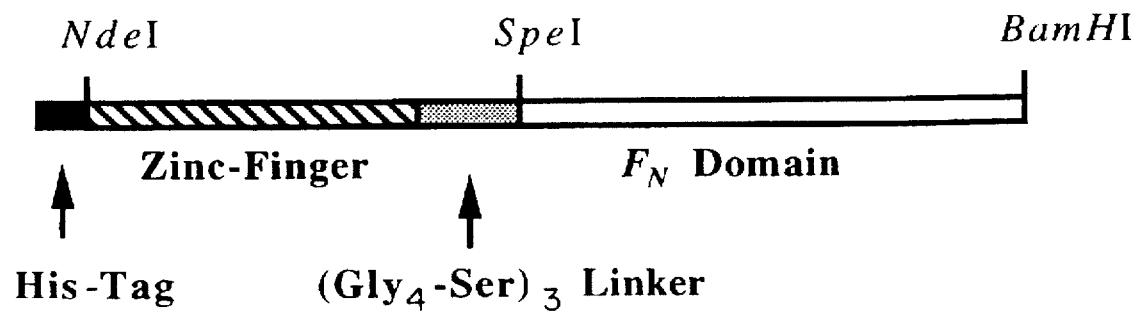

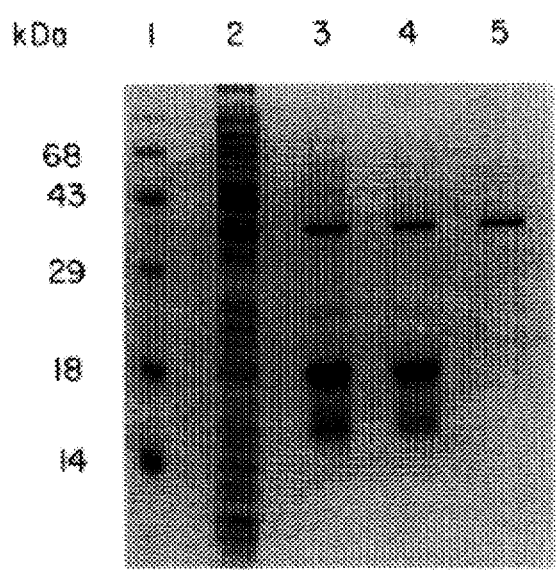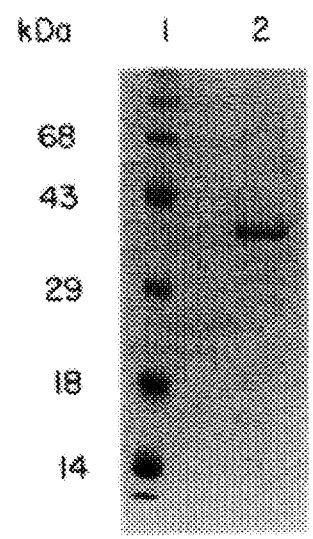

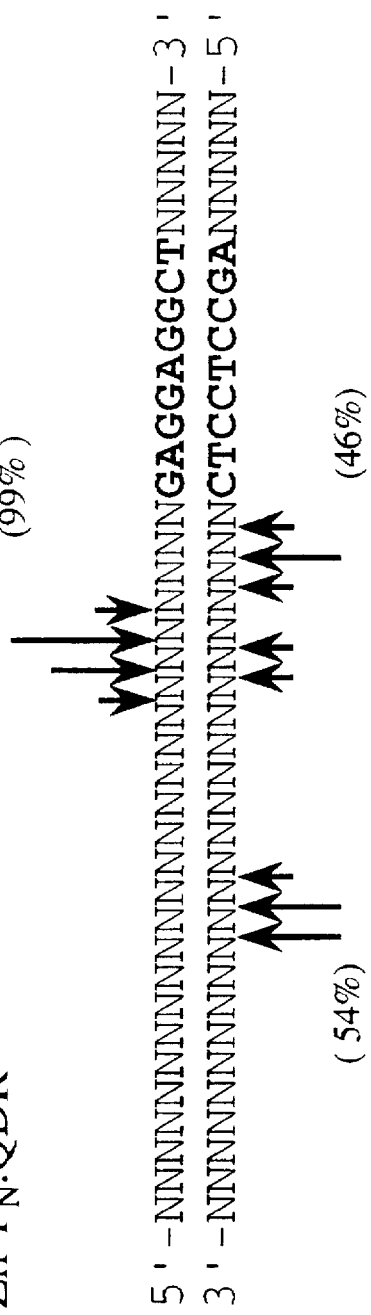
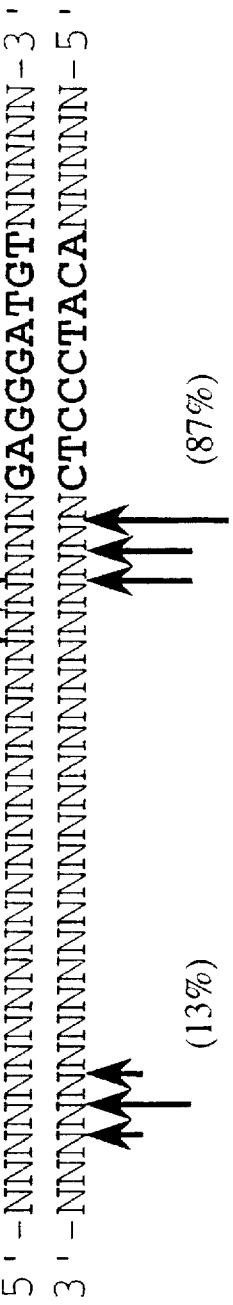

FIG. 14

ZF-QQR-F$_N$

(SEQ ID NO: 21) DNA

SacI                                                     KpnI

5'- GAGCTCCTTTGGATCCAAGCTTCCCGGGGAAGAATTCGAGGAGGCTCTCGAGTCGACTTCCTCTAGAGGTACC -3'
3'- CTCGAGGAAACCTAGGTTCGAAGGGCCCCTTCTTAAGCTCCTCCGAGAGCTCAGCTGAAGGAGATCTCCATGG -5'

(SEQ ID NO: 22) DNA

SacI                                                     KpnI

5'- GAGCTCCTTTGGATCCAAGCTTCCCGGGGAAGAAUUCGAGGAGGCUCUCGAGUCGACUUCCUCUAGAGGUACC -3' RNA
3'- CUCGACCAAACCUAGGUUCGAAGGGCCCCUUCUUAAGCUCCUCCGAGAGCUCAGCUGAAGGAGAUCUCCAUGG -5'

(SEQ ID NO: 23)

ZF-Sp1C-F$_N$

(SEQ ID NO: 24) DNA

BamHI                                                    EcoRI

5'- GGATCCAAGCTTAGCGATCTGCCTGCAGACTCTAGCCAGGGGCGGGGTGGTCTAGTATCGTTCAATGATACTTCATGGAATTC -3'
3'- CCTAGGTTCGAATCGCTAGACGGACGTCTGAGATCGGTCCCCGCCCCACCAGATCATAGCAAGTTACTATGAAGTACCTTAAG -5' DNA

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
      ( A ) LENGTH: 23 amino acids
      ( B ) TYPE: amino acid
      ( D ) TOPOLOGY: linear ( x i ) SEQUENCE DESCRIPTION: SEQ ID NO:1:

```
Tyr  Xaa  Cys  Xaa  Xaa  Cys  Xaa  Xaa  Xaa  Phe  Xaa  Xaa  Xaa  Xaa  Xaa  Leu
1                  5                        10                         15

Xaa  Xaa  His  Xaa  Xaa  Xaa  His
               20
```

( 2 ) INFORMATION FOR SEQ ID NO:2:

( i ) SEQUENCE CHARACTERISTICS:
      ( A ) LENGTH: 24 amino acids
      ( B ) TYPE: amino acid
      ( D ) TOPOLOGY: linear ( x i ) SEQUENCE DESCRIPTION: SEQ ID NO:2:

```
Tyr  Xaa  Cys  Xaa  Xaa  Cys  Xaa  Xaa  Xaa  Phe  Xaa  Xaa  Xaa  Xaa  Xaa  Leu
1                  5                        10                         15

Xaa  Xaa  His  Xaa  Xaa  Xaa  Xaa  His
               20
```

( 2 ) INFORMATION FOR SEQ ID NO:3:

( i ) SEQUENCE CHARACTERISTICS:
      ( A ) LENGTH: 25 amino acids
      ( B ) TYPE: amino acid
      ( D ) TOPOLOGY: linear ( x i ) SEQUENCE DESCRIPTION: SEQ ID NO:3:

```
Tyr  Xaa  Cys  Xaa  Xaa  Cys  Xaa  Xaa  Xaa  Phe  Xaa  Xaa  Xaa  Xaa  Xaa  Leu
1                  5                        10                         15

Xaa  Xaa  His  Xaa  Xaa  Xaa  Xaa  Xaa  His
               20                      25
```

( 2 ) INFORMATION FOR SEQ ID NO:4:

( i ) SEQUENCE CHARACTERISTICS:
        ( A ) LENGTH: 24 amino acids
        ( B ) TYPE: amino acid
        ( D ) TOPOLOGY: linear ( x i ) SEQUENCE DESCRIPTION: SEQ ID NO:4:

```
Tyr Xaa Cys Xaa Xaa Xaa Xaa Cys Xaa Xaa Xaa Phe Xaa Xaa Xaa Xaa
1               5                   10                  15
Leu Xaa Xaa His Xaa Xaa Xaa His
            20
```

( 2 ) INFORMATION FOR SEQ ID NO:5:

( i ) SEQUENCE CHARACTERISTICS:
        ( A ) LENGTH: 25 amino acids
        ( B ) TYPE: amino acid
        ( D ) TOPOLOGY: linear ( x i ) SEQUENCE DESCRIPTION: SEQ ID NO:5:

```
Tyr Xaa Cys Xaa Xaa Xaa Xaa Cys Xaa Xaa Xaa Phe Xaa Xaa Xaa Xaa
1               5                   10                  15
Leu Xaa Xaa His Xaa Xaa Xaa Xaa His
            20                  25
```

( 2 ) INFORMATION FOR SEQ ID NO:6:

( i ) SEQUENCE CHARACTERISTICS:
        ( A ) LENGTH: 26 amino acids
        ( B ) TYPE: amino acid
        ( D ) TOPOLOGY: linear ( x i ) SEQUENCE DESCRIPTION: SEQ ID NO:6:

```
Tyr Xaa Cys Xaa Xaa Xaa Xaa Cys Xaa Xaa Xaa Phe Xaa Xaa Xaa Xaa
1               5                   10                  15
Leu Xaa Xaa His Xaa Xaa Xaa Xaa Xaa His
            20                  25
```

( 2 ) INFORMATION FOR SEQ ID NO:7:

( i ) SEQUENCE CHARACTERISTICS:
        ( A ) LENGTH: 25 amino acids
        ( B ) TYPE: amino acid
        ( D ) TOPOLOGY: linear ( x i ) SEQUENCE DESCRIPTION: SEQ ID NO:7:

```
Tyr Xaa Cys Xaa Xaa Xaa Xaa Cys Xaa Xaa Xaa Phe Xaa Xaa Xaa Xaa
1               5                   10                  15
Xaa Leu Xaa Xaa His Xaa Xaa Xaa His
            20                  25
```

( 2 ) INFORMATION FOR SEQ ID NO:8:

( i ) SEQUENCE CHARACTERISTICS:
        ( A ) LENGTH: 26 amino acids
        ( B ) TYPE: amino acid
        ( D ) TOPOLOGY: linear ( x i ) SEQUENCE DESCRIPTION: SEQ ID NO:8:

```
Tyr Xaa Cys Xaa Xaa Xaa Xaa Cys Xaa Xaa Xaa Phe Xaa Xaa Xaa Xaa
1               5                   10                  15
Xaa Leu Xaa Xaa His Xaa Xaa Xaa Xaa His
            20                  25
```

( 2 ) INFORMATION FOR SEQ ID NO:9:

( i ) SEQUENCE CHARACTERISTICS:
        ( A ) LENGTH: 27 amino acids
        ( B ) TYPE: amino acid
        ( D ) TOPOLOGY: linear ( x i ) SEQUENCE DESCRIPTION: SEQ ID NO:9:

```
Tyr  Xaa  Cys  Xaa  Xaa  Xaa  Xaa  Cys  Xaa  Xaa  Xaa  Phe  Xaa  Xaa  Xaa  Xaa
1                   5                        10                            15

Xaa  Leu  Xaa  Xaa  His  Xaa  Xaa  Xaa  Xaa  Xaa  His
               20                        25
```

( 2 ) INFORMATION FOR SEQ ID NO:10:

( i ) SEQUENCE CHARACTERISTICS:
        ( A ) LENGTH: 23 amino acids
        ( B ) TYPE: amino acid
        ( D ) TOPOLOGY: linear ( x i ) SEQUENCE DESCRIPTION: SEQ ID NO:10:

```
Phe  Xaa  Cys  Xaa  Xaa  Cys  Xaa  Xaa  Xaa  Phe  Xaa  Xaa  Xaa  Xaa  Xaa  Leu
1                   5                        10                            15

Xaa  Xaa  His  Xaa  Xaa  Xaa  His
               20
```

( 2 ) INFORMATION FOR SEQ ID NO:11:

( i ) SEQUENCE CHARACTERISTICS:
        ( A ) LENGTH: 24 amino acids
        ( B ) TYPE: amino acid
        ( D ) TOPOLOGY: linear ( x i ) SEQUENCE DESCRIPTION: SEQ ID NO:11:

```
Phe  Xaa  Cys  Xaa  Xaa  Cys  Xaa  Xaa  Xaa  Phe  Xaa  Xaa  Xaa  Xaa  Xaa  Leu
1                   5                        10                            15

Xaa  Xaa  His  Xaa  Xaa  Xaa  Xaa  His
               20
```

( 2 ) INFORMATION FOR SEQ ID NO:12:

( i ) SEQUENCE CHARACTERISTICS:
        ( A ) LENGTH: 25 amino acids
        ( B ) TYPE: amino acid
        ( D ) TOPOLOGY: linear ( x i ) SEQUENCE DESCRIPTION: SEQ ID NO:12:

```
Phe  Xaa  Cys  Xaa  Xaa  Cys  Xaa  Xaa  Xaa  Phe  Xaa  Xaa  Xaa  Xaa  Xaa  Leu
1                   5                        10                            15

Xaa  Xaa  His  Xaa  Xaa  Xaa  Xaa  Xaa  His
               20                        25
```

( 2 ) INFORMATION FOR SEQ ID NO:13:

( i ) SEQUENCE CHARACTERISTICS:
        ( A ) LENGTH: 24 amino acids
        ( B ) TYPE: amino acid
        ( D ) TOPOLOGY: linear ( x i ) SEQUENCE DESCRIPTION: SEQ ID NO:13:

```
Phe  Xaa  Cys  Xaa  Xaa  Xaa  Cys  Xaa  Xaa  Xaa  Phe  Xaa  Xaa  Xaa  Xaa  Xaa
1                   5                        10                            15

Leu  Xaa  Xaa  His  Xaa  Xaa  Xaa  His
               20
```

( 2 ) INFORMATION FOR SEQ ID NO:14:

( i ) SEQUENCE CHARACTERISTICS:
        ( A ) LENGTH: 25 amino acids
        ( B ) TYPE: amino acid
        ( D ) TOPOLOGY: linear ( x i ) SEQUENCE DESCRIPTION: SEQ ID NO:14:

```
Phe Xaa Cys Xaa Xaa Xaa Cys Xaa Xaa Xaa Phe Xaa Xaa Xaa Xaa Xaa
1               5                   10                  15

Leu Xaa Xaa His Xaa Xaa Xaa Xaa His
            20                  25
```

( 2 ) INFORMATION FOR SEQ ID NO:15:

( i ) SEQUENCE CHARACTERISTICS:
        ( A ) LENGTH: 26 amino acids
        ( B ) TYPE: amino acid
        ( D ) TOPOLOGY: linear ( x i ) SEQUENCE DESCRIPTION: SEQ ID NO:15:

```
Phe Xaa Cys Xaa Xaa Xaa Cys Xaa Xaa Xaa Phe Xaa Xaa Xaa Xaa Xaa
1               5                   10                  15

Leu Xaa Xaa His Xaa Xaa Xaa Xaa Xaa His
            20                      25
```

( 2 ) INFORMATION FOR SEQ ID NO:16:

( i ) SEQUENCE CHARACTERISTICS:
        ( A ) LENGTH: 25 amino acids
        ( B ) TYPE: amino acid
        ( D ) TOPOLOGY: linear ( x i ) SEQUENCE DESCRIPTION: SEQ ID NO:16:

```
Phe Xaa Cys Xaa Xaa Xaa Xaa Cys Xaa Xaa Xaa Phe Xaa Xaa Xaa Xaa
1               5                   10                  15

Xaa Leu Xaa Xaa His Xaa Xaa Xaa His
            20                  25
```

( 2 ) INFORMATION FOR SEQ ID NO:17:

( i ) SEQUENCE CHARACTERISTICS:
        ( A ) LENGTH: 26 amino acids
        ( B ) TYPE: amino acid
        ( D ) TOPOLOGY: linear ( x i ) SEQUENCE DESCRIPTION: SEQ ID NO:17:

```
Phe Xaa Cys Xaa Xaa Xaa Xaa Cys Xaa Xaa Xaa Phe Xaa Xaa Xaa Xaa
1               5                   10                  15

Xaa Leu Xaa Xaa His Xaa Xaa Xaa Xaa His
            20                      25
```

( 2 ) INFORMATION FOR SEQ ID NO:18:

( i ) SEQUENCE CHARACTERISTICS:
        ( A ) LENGTH: 27 amino acids
        ( B ) TYPE: amino acid
        ( D ) TOPOLOGY: linear ( x i ) SEQUENCE DESCRIPTION: SEQ ID NO:18:

```
Phe Xaa Cys Xaa Xaa Xaa Xaa Cys Xaa Xaa Xaa Phe Xaa Xaa Xaa Xaa
1               5                   10                  15

Xaa Leu Xaa Xaa His Xaa Xaa Xaa Xaa Xaa His
            20                          25
```

( 2 ) INFORMATION FOR SEQ ID NO:19:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:19:

```
NNNNNNNNN NNNNNNNNN NNNNNGAGGA GGCTNNNNN                                      39
```

( 2 ) INFORMATION FOR SEQ ID NO:20:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:20:

```
NNNNNNNNN NNNNNNNNN NNNNNGAGGG ATGTNNNNN                                      39
```

( 2 ) INFORMATION FOR SEQ ID NO:21:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
GAGCTCCTTT GGATCCAAGC TTCCCGGGGA AGAATTCGAG GAGGCTCTCG AGGTCGACTT             60
CCTCTAGAGG TACC                                                              74
```

( 2 ) INFORMATION FOR SEQ ID NO:22:

( i ) SEQUENCE CHARACTERISTICS:
        ( A ) LENGTH: 74 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:22:

```
GAGCTCCTTT GGATCCAAGC TTCCCGGGGA AGAATTCGAG GAGGCTCTCG AGGTCGACTT             60
CCTCTAGAGG TACC                                                              74
```

( 2 ) INFORMATION FOR SEQ ID NO:23:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
CUCGACCAAA CCUAGGUUCG AAGGGCCCCU UCUUAAGCUC CUCCGAGAGC UCCAGCUGAA             60
GGAGAUCUCC AUGG                                                              74
```

( 2 ) INFORMATION FOR SEQ ID NO:24:

( i ) SEQUENCE CHARACTERISTICS:
        ( A ) LENGTH: 87 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:24:

GGATCCAAGC TTAGCGATCT GCCTGCAGGT CGACTCTAGC CAGGGGCGGG GTGGTCTAGT 60

ATCGTTCAAT GATACTTCAT GGAATTC 87

( 2 ) INFORMATION FOR SEQ ID NO:25:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

CCCCTGAAGG AGATATACAT ATG 23

( 2 ) INFORMATION FOR SEQ ID NO:26:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

GGACTAGTCC CTTCTTATTC TGGTG 25

( 2 ) INFORMATION FOR SEQ ID NO:27:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:27:

Gly Gly Gly Gly Ser Gly Gly Gly Gly Ser Gly Gly Gly Gly Ser
1               5                   10                  15

( 2 ) INFORMATION FOR SEQ ID NO:28:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

CTGACGGGGG CCAA 14

( 2 ) INFORMATION FOR SEQ ID NO:29:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

CTAGTTGGCC CCCGT 15

( 2 ) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (x i) SEQUENCE DESCRIPTION: SEQ ID NO:30:

CTAGACGGGG GAGGCGGCAG TCAA 24

(2) INFORMATION FOR SEQ ID NO:31:

(i) SEQUENCE CHARACTERISTICS:
(A) LENGTH: 24 base pairs
(B) TYPE: nucleic acid
(C) STRANDEDNESS: single
(D) TOPOLOGY: linear (x i) SEQUENCE DESCRIPTION: SEQ ID NO:31:

CTAGTTGACT GCCGCCTCCC CCGT 24

(2) INFORMATION FOR SEQ ID NO:32:

(i) SEQUENCE CHARACTERISTICS:
(A) LENGTH: 5 amino acids
(B) TYPE: amino acid
(D) TOPOLOGY: linear (x i) SEQUENCE DESCRIPTION: SEQ ID NO:32:

Gly Gly Gly Gly Ser
1               5

(2) INFORMATION FOR SEQ ID NO:33:

(i) SEQUENCE CHARACTERISTICS:
(A) LENGTH: 39 base pairs
(B) TYPE: nucleic acid
(C) STRANDEDNESS: single
(D) TOPOLOGY: linear (x i) SEQUENCE DESCRIPTION: SEQ ID NO:33:

CTAGACGGGG GAGGCGGCAG TGGAGGTGGC GGATCACAA 39

(2) INFORMATION FOR SEQ ID NO:34:

(i) SEQUENCE CHARACTERISTICS:
(A) LENGTH: 39 base pairs
(B) TYPE: nucleic acid
(C) STRANDEDNESS: single
(D) TOPOLOGY: linear (x i) SEQUENCE DESCRIPTION: SEQ ID NO:34:

CTAGTTGTGA TCCGCCACCT CCACCGTCGC CTCCCCCGT 39

(2) INFORMATION FOR SEQ ID NO:35:

(i) SEQUENCE CHARACTERISTICS:
(A) LENGTH: 10 amino acids
(B) TYPE: amino acid
(D) TOPOLOGY: linear (x i) SEQUENCE DESCRIPTION: SEQ ID NO:35:

Gly Gly Gly Gly Ser Gly Gly Gly Gly Ser
1               5                   10

GENERAL METHOD TO CLONE HYBRID RESTRICTION ENDONUCLEASES USING LIG GENE

This application is a continuation-in-part of U.S. application Ser. No. 08/346,293, filed Nov. 23, 1994, issued as U.S. Pat. No. 5,487,994, which is a continuation-in-part of Ser. No. 08/126,564, filed Sep. 27, 1993, issued as U.S. Pat. No. 5,436,150, Jul. 25, 1995, which is a continuation-in-part of U.S. application Ser. No. 08/017,493, filed Feb. 12, 1993, abandoned, which is a continuation-in-part of U.S. application Ser. No. 07/862,831, Apr. 3, 1992, issued as U.S. Pat. No. 5,356,802.

This patent application was supported in part by grant GM 42140 from the National Institutes of Health and by grant MCB-9415861 from the National Science Foundation. The Government has certain rights in the invention.

BACKGROUND OF THE INVENTION

1. Field of the Invention

The present invention relates to hybrid genes which encode hybrid restriction endonucleases. The hybrid restriction endonucleases are designed to recognize DNA at given base sites and to enzymatically cleave the DNA at distant sites.

More specifically, the present invention relates to a method for cloning hybrid restriction endonucleases and to a method for enzymatically inactivating a target DNA.

2. Description of the Related Art

Since their discovery nearly 25 years ago (1), Type II restriction enzymes have played a crucial role in the development of the recombinant DNA technology and the field of molecular biology. The Type II restriction (R) endonucleases and modification (M) methylases are relatively simple bacterial enzymes that recognize specific sequences in duplex DNA. While the former cleave DNA, the latter methylate adenine or cytosine residues within the recognition site so as to protect the host-genome against cleavage by the former. So far, over 2500 restriction and modification enzymes have been identified and these are found in widely diverse organisms (2). These enzymes fall into numerous "isoschizomer" (identically cleaving) groups with about 200 sequence-specificities.

Discovery of new enzymes involves tedious and time-consuming effort that requires extensive screening of bacteria and other microorganisms (3). Even when one finds a new enzyme, more often than not, it falls into the already-discovered isoschizomer groups. Furthermore, most naturally occurring restriction enzymes recognize sequences that are 4–6 bp long. Although these enzymes are very useful in manipulating recombinant DNA, they are not suitable for producing large DNA segments. For example, restriction enzymes that recognize DNA sequences 6 bp long, result in cuts as often as every 4096 bases. In many instances, it is preferable to have fewer but longer DNA strands, especially during genome mapping. Rare cutters like NotI, that recognizes 8 bp-long sequences, cut human DNA (which contains about 3 billion bp) every 65536 bases on average. So far, only a few endonucleases with recognition sequences longer than 6 bp (rare cutters) have been identified (New England Biolabs catalog).

R-M (restriction-modification) systems appear to have a single biological function—namely, to protect cells from infection by foreign DNA that would otherwise destroy them. The phage genomes are usually small. It stands to reason, then, that bacteria select for R-M systems with small recognition sites (4–6 bp) because these sites occur more frequently in the phages. Therefore, a long term goal in the field of restriction-modification enzymes has been to generate restriction endonucleases with longer recognition sites by mutating or engineering existing enzymes (3).

The FokI restriction endonuclease from *Flavobacterium okeanokoites* belongs to the Type IIS class of endonucleases. FokI recognizes the asymmetric sequence 5'-GGATG-3' and cleaves double-stranded DNA at staggered sites 9 and 13 nucleotides away from the recognition site. The cloning and sequencing of the FokI restriction-modification system have been reported. Several research groups have purified FokI endonuclease and characterized its properties. Previous reports by the present inventor on proteolytic fragments of FokI endonuclease using trypsin have revealed an N-terminal DNA-binding domain and a C-terminal catalytic domain with non-specific DNA cleavage activity (4–7). These reports have suggested that the two domains are connected by a linker region which is susceptible to cleavage by trypsin. The present inventor has also shown that insertion of four (or seven) codons between the recognition and cleavage domains of FokI can alter the cleavage distance of FokI within its substrate.

Recently, Waugh and Sauer have shown that single amino acid substitutions uncouple the DNA-binding and strand scission activities of FokI endonuclease (28). Furthermore, they have obtained a novel class of FokI restriction mutants that cleave hemi-methylated DNA substrates (29). The modular structure of FokI suggested that it may be feasible to construct hybrid endonucleases with novel sequence-specificity by linking other DNA-binding proteins to the cleavage domain of FokI endonuclease. Recently, the present inventor reported the construction of the first "chimeric" restriction endonuclease by linking the Ubx homeo domain to the cleavage domain of FokI (8).

To further probe the linker region, the present inventor constructed several insertion and deletion mutants of FokI endonuclease. A detailed description of the process for making and using and the properties of these mutants are disclosed in U.S. patent application Ser. No. 08/346,293, allowed, the entire contents of which are hereby incorporated by reference and relied upon.

Unlike the Ubx homeo domain, zinc finger proteins, because of their modular structure, offer a better framework for designing chimeric restriction enzymes with tailor-made sequence-specificities. The Cys$_2$His$_2$ zinc finger proteins are a class of DNA-binding proteins that contain sequences of the form (Tyr,Phe)-Xaa-Cys-Xaa$_{2-4}$-Cys-Xaa$_3$-Phe-Xaa$_5$-Leu-Xaa$_2$-His-Xaa$_{3-5}$-His (SEQ ID NO:1–18) usually in tandem arrays (9). Each of these sequences binds a zinc(ii) ion to form the structural domain termed a zinc finger. These proteins, like many sequence-specific DNA-binding proteins, bind to the DNA by inserting an α-helix into the major groove of the double helix (10).

The crystallographic structure of the three zinc finger domain of zif268 bound to a cognate oligonucleotide reveals that each finger interacts with a triplet within the DNA substrate. Each finger, because of variations of certain key amino acids from one zinc finger to the next, makes its own unique contribution to DNA-binding affinity and specificity.

The zinc fingers, because they appear to bind as independent modules, can be linked together in a peptide designed to bind a predetermined DNA site. Although, more recent studies suggest that the zinc finger—DNA recognition is more complex than originally perceived (11,12), it still appears that zinc finger motifs will provide an excellent framework for designing DNA-binding proteins with a variety of new sequence-specificities.

In theory, one can design a zinc finger for each of the 64 possible triplet codons and using a combination of these fingers, one could design a protein for sequence-specific recognition of any segment of DNA. Studies to understand the rules relating to zinc finger sequences/DNA-binding preferences and redesigning of DNA-binding specificities of zinc finger proteins are well underway (13–15).

An alternative approach to the design of zinc finger proteins with new specificities involves the selection of desirable mutants from a library of randomized fingers displayed on phage (16–20). The ability to design or select zinc fingers with desired specificity implies that DNA-binding proteins containing zinc fingers will be made to order. Therefore, we reasoned that one could design "artificial" nucleases that will cut DNA at any preferred site by making fusions of zinc finger proteins to the cleavage domain of FokI endonuclease. We thus undertook the deliberate creation of zinc finger hybrid restriction enzymes, the cloning of the hybrid enzymes and the characterization of their DNA cleavage properties.

One of the main difficulties in cloning or overproducing restriction enzymes is their potential lethality. The restriction enzymes can enzymatically attack and destroy the host DNA. This is circumvented by first cloning a methylase gene (M). The methylase gene modifies the restriction enzyme sites and provides protection against chromosomal cleavage. A restriction endonuclease gene (R) is then introduced into the host on a separate compatible plasmid.

Our work on hybrid restriction endonuclease genes has indicated that they are likewise lethal, since there are no corresponding methylase genes available to protect the host genome from cleavage by the hybrid endonuclease. We now report on a method for cloning the genes for hybrid restriction endonucleases and on a method for using nucleases to enzymatically destroy a target DNA. Furthermore, the method for cloning can be used to clone either mutant or wild type restriction endonucleases.

SUMMARY OF THE INVENTION

The present invention reveals methods for cloning restriction endonucleases by the co-expression of ligase and for inducing nucleases to enzymatically inactivate a target DNA, thereby destroying the target DNA.

The method for cloning hybrid restriction endonucleases requires:

a) preparing a first plasmid containing a gene encoding a DNA ligase;

b) transfecting cells with the first plasmid so that DNA ligase is produced;

c) preparing a second compatible plasmid containing a gene encoding a hybrid restriction endonuclease;

d) transfecting the cells with the second plasmid; and e) cloning the cells.

Both prokaryotic cells, e.g., $E.\ coli$ cells, and eukaryotic cells, e.g., plant cells and mammalian cells, can be used in this method. Furthermore, mutant strains of cells that produce increased levels of DNA ligase can be used in this method.

Examples of genes encoding a hybrid restriction endonuclease that can be used in the method include ZF-QDR-$F_N$, ZF-Sp1C-$F_N$, ZF-QNR-$F_N$, ZF-QQR-$F_N$ and ZFHD1-$F_N$.

The method for enzymatically inactivating a target DNA requires:

a) preparing a plasmid, virus, phage or any other delivery vehicle such as a liposome containing a gene encoding a nuclease, wherein the nuclease specifically recognizes and enzymatically inactivates the target DNA;

b) delivering the plasmid, virus, phage or any other delivery vehicle such as a liposome containing the gene encoding a nuclease into cells;

c) inducing the cells to produce the nuclease; and d) enzymatically inactivating the target DNA.

Both prokaryotic cells, e.g., $E.\ coli$ cells, and eukaryotic cells, e.g., plant cells and mammalian cells, can be used in this method. Furthermore, either naturally occurring endonucleases or engineered hybrid nucleases can be used in this method. The use of a hybrid restriction endonuclease is preferred. Examples of genes encoding a hybrid restriction endonuclease that can be used in the method include ZF-QDR-$F_N$, ZF-Sp1C-$F_N$, ZF-QNR-$F_N$, ZF-QQR-$F_N$ and ZFHD1-$F_N$.

Furthermore, genes encoding the hybrid restriction nucleases with appropriate control elements (e.g., viral promoters) can be integrated into the chromosome of cells using appropriate plasmid, virus, phage or any other delivery vehicle such as a liposome containing a gene encoding a nuclease. Thus, a delivery vehicle is defined as any plasmid, virus, phage or any other physical structure such as a liposome which is able to contain a gene. Exposure to the appropriate virus will induce the production of the hybrid restriction endonuclease and stop the propagation of the virus.

In addition, the target DNA may be DNA exogenous to DNA of the cells or a DNA endogenous to DNA of the cells. The exogenous DNA target may be a self-replicating DNA, linear or circular, or a DNA intermediate of an RNA tumor virus. The endogenous DNA target may be the chromosomal DNA of the cells.

BRIEF DESCRIPTION OF THE DRAWINGS

FIGS. 1A and 1B show the construction of expression vectors of ZF-$F_N$. FIG. 1A shows the structure of the plasmid pET-15b:ZF-$F_N$. FIG. 1B shows the map of the ZF-$F_N$ gene. The methods to construct the overproducer clones of ZF-$F_N$ and the protein purification procedures are described in detail herein and elsewhere (26,35). ZF-$F_N$ is a generic abbreviation for a fusion product of zinc fingers (ZF) and the FokI endonuclease domain ($F_N$).

FIG. 2 shows the purification of ZF-$F_N$ hybrid enzymes. FIG. 2A shows the SDS/PAGE profiles at each step in the purification of ZF-QNR-$F_N$ hybrid enzyme. ZF-QNR-$F_N$ is a specific abbreviation for a fusion product between the eukaryotic transcription factor Sp1 (a specific zinc finger) and the FokI endonuclease domain ($F_N$). QNR indicates the sequence specific contact residues, that is, glutamine-asparagine-arginine, for the zinc finger recognition domain of the fusion product. Lane 1 shows protein standards; lane 2 shows crude extract from induced cells; lane 3 shows the results of purification after His-bind resin column chromatography; lane 4 shows the results after SP-sepharose column chromatography; and lane 5 shows the results after gel filtration column chromatography.

FIG. 2B shows the SDS/PAGE profile of ZF-QDR-$F_N$ hybrid enzyme. ZF-QDR-$F_N$ is a specific abbreviation for a fusion product between the designed consensus protein CP (a specific zinc finger) and the FokI endonuclease domain ($F_N$). QDR indicates the sequence specific contact residues, that is, glutamine-aspartic acid-arginine, for the zinc finger recognition domain of the fusion product. Lane 1 shows protein standards and lane 2 the purified ZF-QDR-$F_N$ fusion protein.

The substrate cleaves into 5.5 kb and 43 kb fragments (open arrows). Lane 4 shows λ DNA digested with ZF-QNR-$F_N$. The substrate cleaves into ~9.5 kb and ~39 kb fragments (closed arrows). Lane 5 shows high molecular weight markers from BRL (top to bottom: 48.5, 38.4, 33.5, 29.9, 24.8, 22.6, 19.4, 17.0, 15.0., 12.2, 10.1, 8.6 and 8.3 kb respectively). Weaker bands result from cleavage at the minor DNA-binding sites. tRNA of the reaction mixture runs outside the region shown in the figure.

Figure 3:
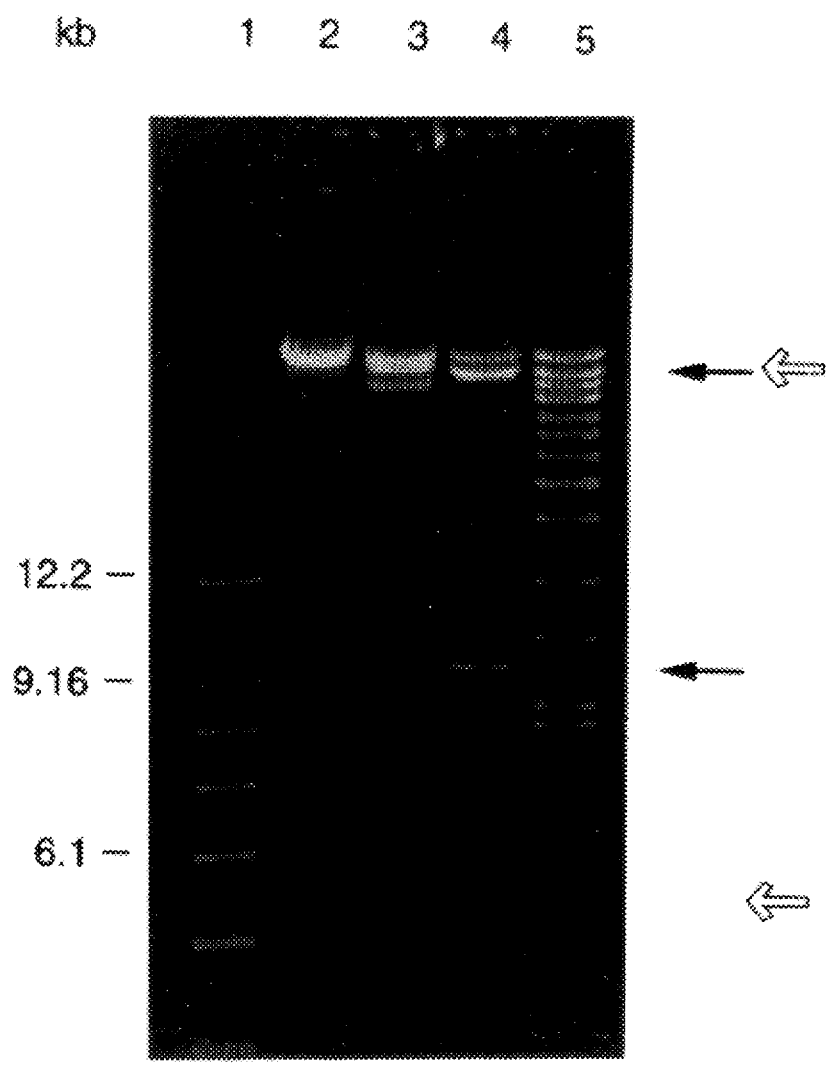
FIG. 3 shows the cleavage of λ DNA (48.5 Kb) substrate by the hybrid enzymes, ZF-$F_N$. Lane 1 shows a kb ladder; lane 2 shows λ DNA; and lane 3 shows λ DNA digested with the hybrid ZF-QDR-$F_N$.
Figure 4A:
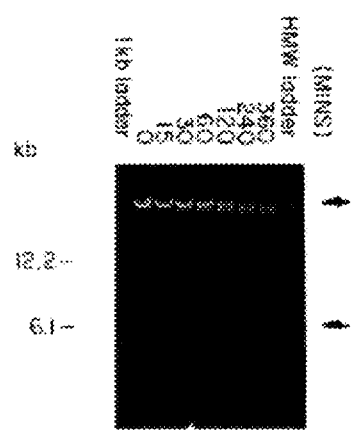
Figure 4B:
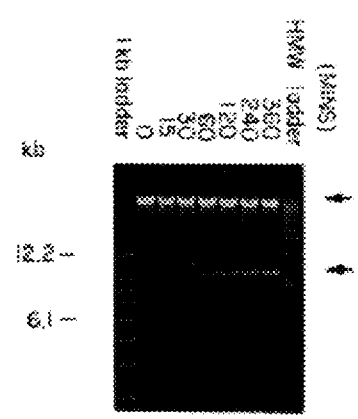
Figure 4C:
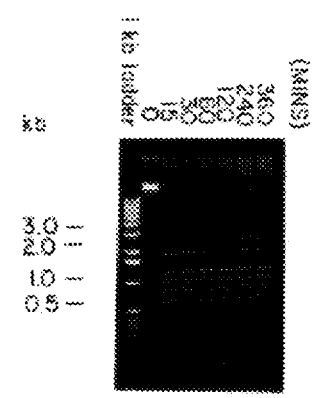

FIG. 4 shows the kinetics of cleavage of the lambda DNA substrate. FIG. 4A shows the cleavage of λ DNA substrate by ZF-QDR-$F_N$. FIG. 4B shows the cleavage of λ DNA substrate by ZF-QNR-$F_N$. FIG. 4C shows the cleavage of λ DNA substrate by wild-type FokI endonuclease. The reaction conditions were as described for FIG. 3. Aliquots (12 µl each) were removed from a 90 µl reaction mixture at 0, 15, 30, 60, 120, 240 and 360 minutes respectively. The products were analyzed by agarose gel electrophoresis. The arrows indicate the major cleavage products of the lambda DNA substrate. The lambda DNA was digested with 18 units of wild-type FokI in a volume of 90 µl using NEB (New England Biolabs) buffer.

Figure 5A:
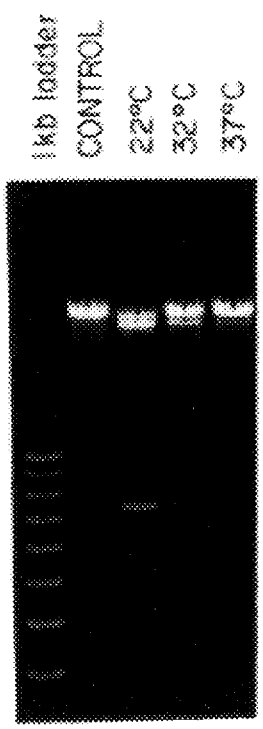
Figure 5B:
Figure 5C:
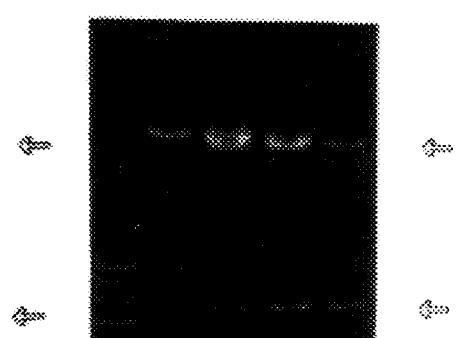

FIG. 5 shows the effect of reaction conditions on the cleavage activity of the hybrid enzyme, ZF-QNR-$F_N$. FIG. 5A shows the effect of temperature; FIG. 5B shows the effect of KCl concentration; and FIG. 5C shows the effect of $MgCl_2$ concentration on the cleavage activity of the hybrid enzyme, ZF-QNR-$F_N$. The reaction conditions were as described for FIG. 3 except for the variables which are shown on the top of the figures. Arrows show the major cleavage products from the lambda DNA substrate.

Figure 6A:
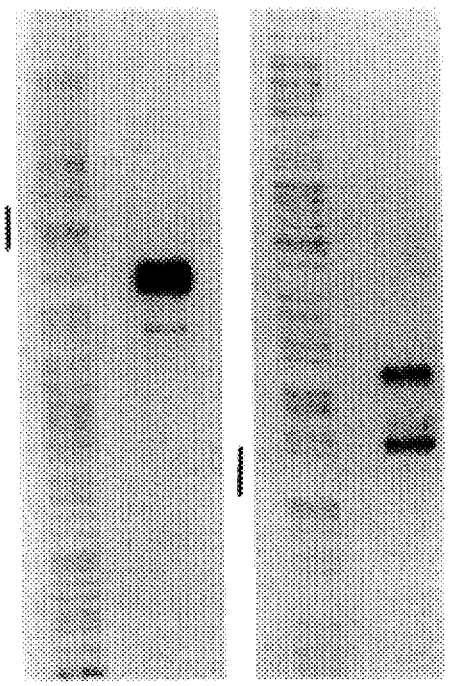
Figure 6B:
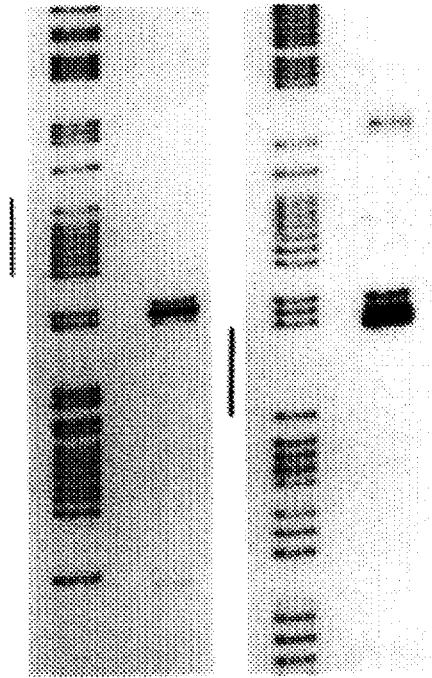

FIG. 6 shows an analysis of the distance of cleavage from the recognition site by ZF-$F_N$ hybrid enzymes. FIGS. 6A and 6B show the cleavage products from the substrates by ZF-QDR-$F_N$ and ZF-QNR-$F_N$, respectively. Lane 1 and 4 show the (G+A) sequencing reaction; lane 2 shows substrates containing $^{32}$P-label on the top strand, 5'-GAG GAG GCT-3' and 5'-GAG GGA TGT-3', respectively; lane 3 shows ZF-$F_N$ digestion products; lane 5 shows substrates containing $^{32}$P-labeled on the bottom strand, 5'-AGC CTC CTC-3' and 5'-ACA TCC CTC-3', respectively; and lane 6 shows ZF-$F_N$ digestion products. The location of the DNA-binding sites for the hybrid enzymes are indicated by vertical lines.

FIGS. 6C and 6D show the map of the major recognition and cleavage site(s) of ZF-QDR-$F_N$ and ZF-QNR-$F_N$ hybrid enzymes on DNA (SEQ ID NO:19 and SEQ ID NO:20), respectively. The recognition site is shown by bold type and the site(s) of cleavage are indicated by arrows. The percent cleavage at each location are shown in brackets. ZF-QDR-$F_N$ is indicated as Zif-QDR-$F_N$ in FIG. 6C and ZF-QNR-$F_N$ is indicated as Zif-QNR-$F_N$ in FIG. 6D. Thus, the designations ZF and Zif are interchangeable.

Figure 7:
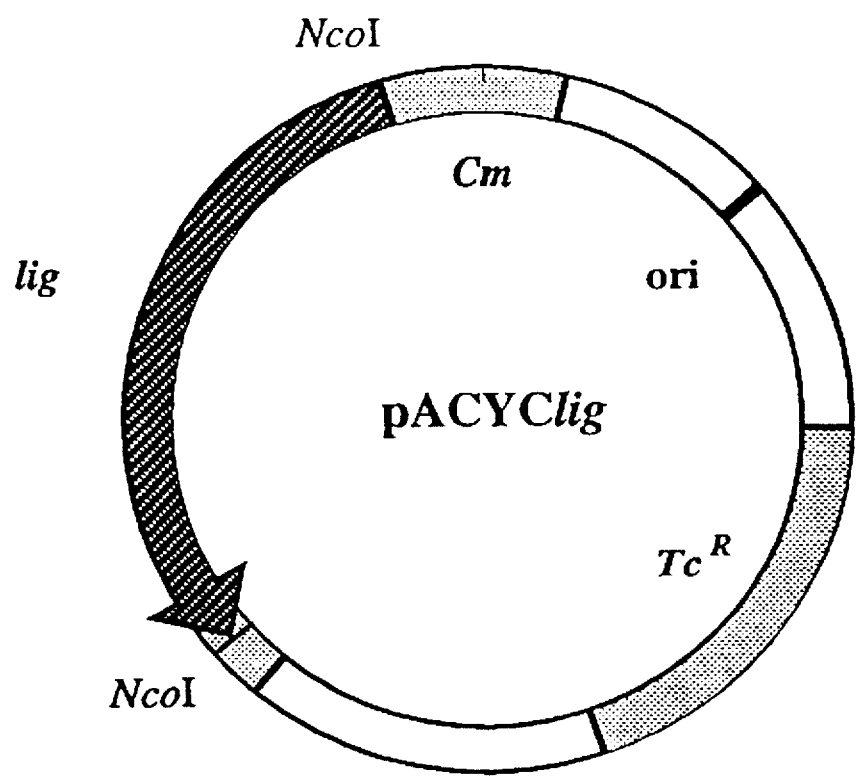

FIG. 7 shows the structure of plasmid pACYC lig. The *E. coli* ligase gene, lig, was inserted into the NcoI site of plasmid pACYC184.

Figures 8A, 8B, 8C:
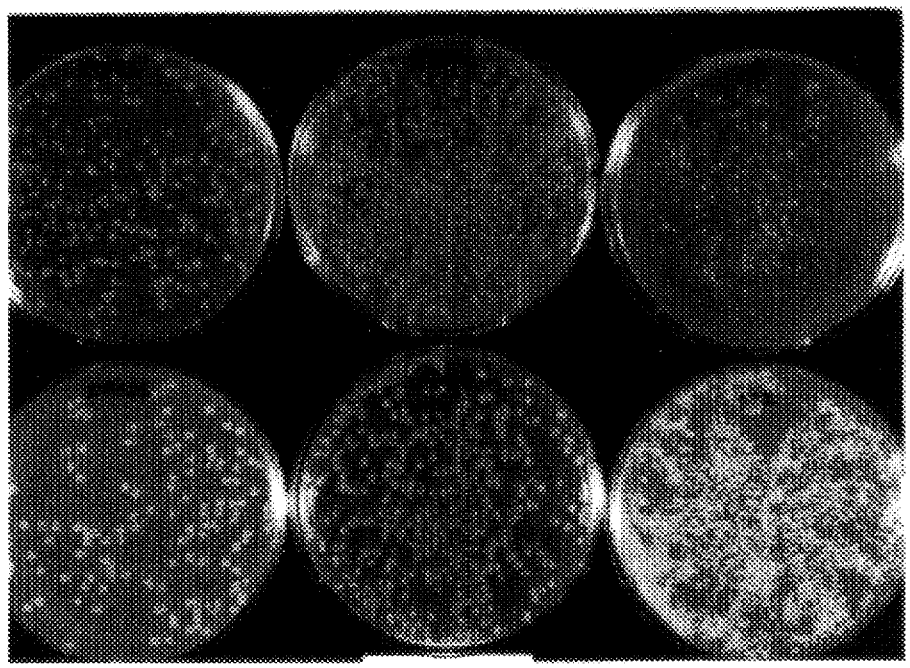

FIG. 8 shows a comparison of transformation efficiency of two different hybrid endonuclease genes, pET-15b:ZFHD1-$F_N$ and pET-15b:ZF-QQR-$F_N$, in BL21 (DE3) cells, with and without pACYC lig. The top panel shows BL21 (DE3) (pACYC lig) cells and the bottom panel shows BL21 (DE3) cells. Column A shows pET-15ZFHD1-$F_N$; Column B shows pET-15b:ZF-QQR-$F_N$; and Column C shows the control pTZ19R. The plasmid pTZ19R (pTZ) that does not carry a hybrid endonuclease gene was used as standard control to compare the efficiency of transformation of the competent cells. BL21 (DE3) (pACYC lig) transforms at about 5–10 fold lower efficiency as compared to BL21 (DE3) cells.

ZFHD1-$F_N$ is a specific abbreviation for a fusion product of the eukaryotic transcription factor Sp1 (a specific zinc finger), the Ubx homeo domain (HD) and the FokI endonuclease domain ($F_N$). ZF-QQR-$F_N$ is a specific abbreviation for a fusion product between the eukaryotic transcription factor Sp1 (a specific zinc finger) and the FokI endonuclease domain ($F_N$). QQR indicates the sequence specific contact residues, that is, glutamine-glutamine-arginine, for the zinc finger recognition domain of the fusion product.

Figure 9:
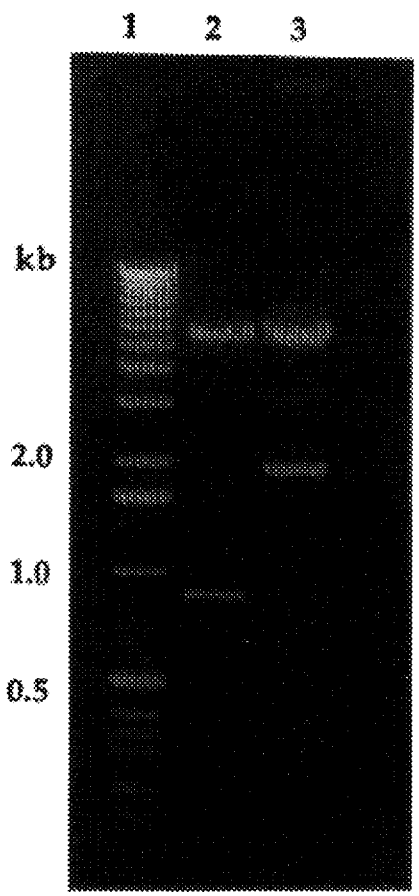

FIG. 9 shows the characterization of pET-15b plasmid containing the ZF-QDR-$F_N$ hybrid gene from RR1 and BL21 (DE3) cells. The plasmids were digested with NdeI and XhoI to excise the ZF-QDR-$F_N$ hybrid gene. Only mutants which are ~0.9 kb larger than the original construct were obtained from the BL21 (DE3) cells. This is consistent with the jumping in of IS1 element to disrupt the hybrid gene that is lethal to the cells. See, for example, Birkenbihl et al. (37). Lane 1 shows a kb ladder; lane 2 shows a plasmid from RR1 cells; and lane 3 shows a plasmid from BL21 (DE3) cells.

ZF-QDR-$F_N$ is a specific abbreviation for a fusion product between the eukaryotic transcription factor Sp1 (a specific zinc finger) and the FokI endonuclease domain ($F_N$). QDR indicates the sequence specific contact residues, that is, glutamine-aspartic acid-arginine, for the zinc finger recognition domain of the fusion product.

Figure 10A:
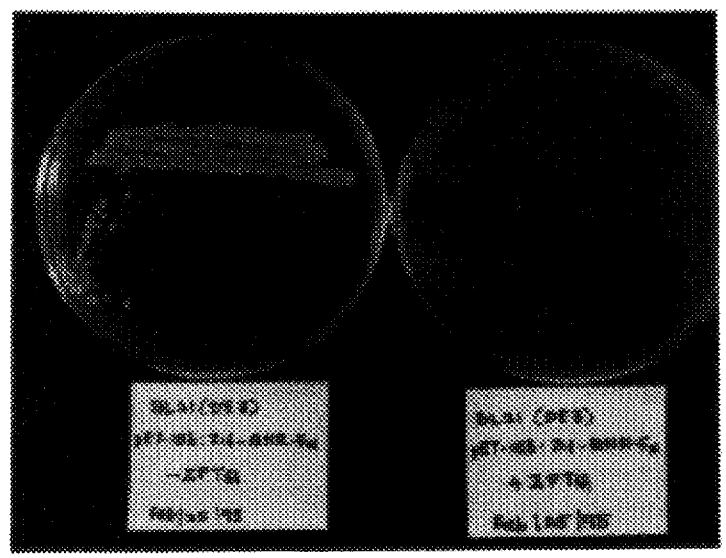
Figure 10B:
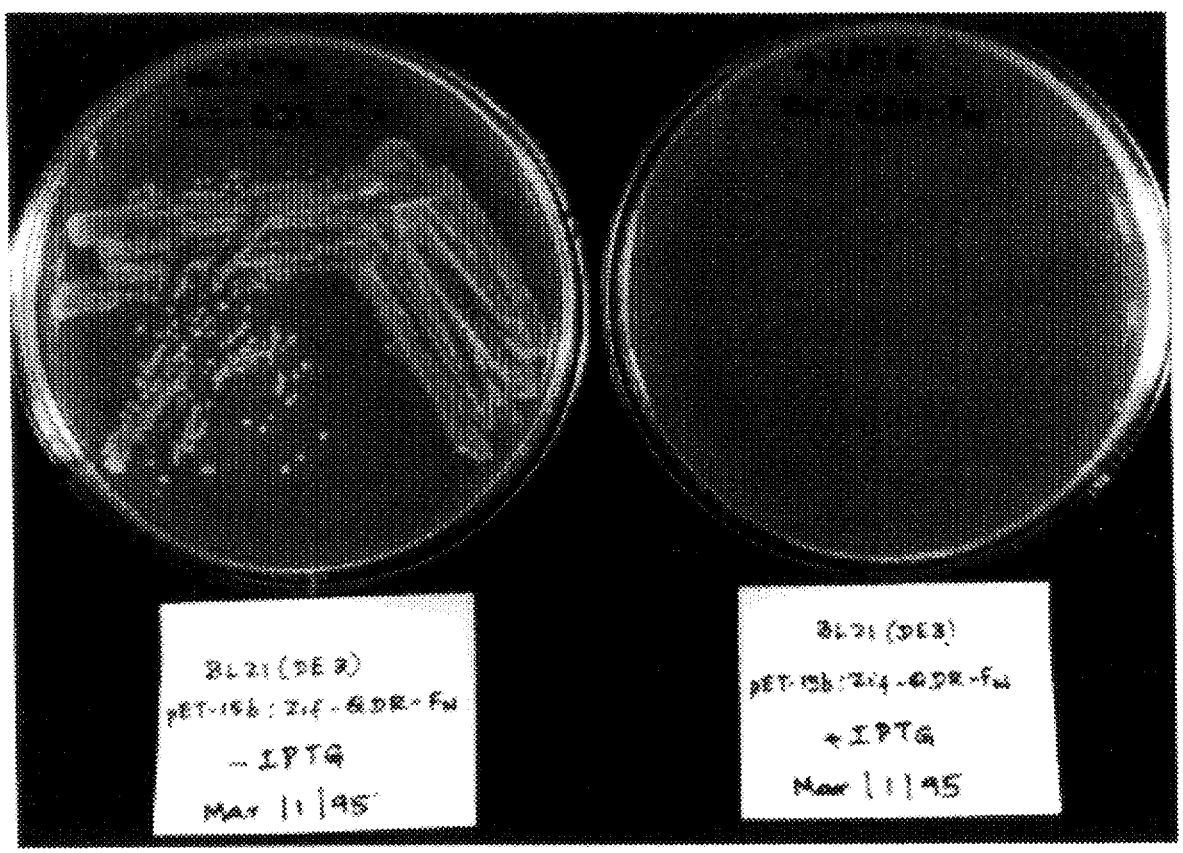

FIGS. 10A and 10B show BL21 (DE3) (pACYC lig) cells with plasmids that carry hybrid endonuclease genes grown on LB-Amp-Tet plates (Luria-Bertocni media containing 50 µg/ml ampicillin and 20 µg/ml tetracycline) with and without isopropyl β-D-thiogalactoside (IPTG). FIG. 10A shows BL21 (DE3) (pACYC lig) pET-15b:ZF-QNR-$F_N$) cells: Left, –IPTG and Right, +IPTG. FIG. 10B shows BL21 (DE3) (pACYC lig) (pET-15b:ZF-QDR-$F_N$) cells: Left, –IPTG and Right, +IPTG.

ZF-QNR-$F_N$ is indicated as Zif-QNR-$F_N$ in FIG. 10A and ZF-QDR-$F_N$ is indicated as Zif-QDR-$F_N$ in FIG. 10B.

Figure 11A:
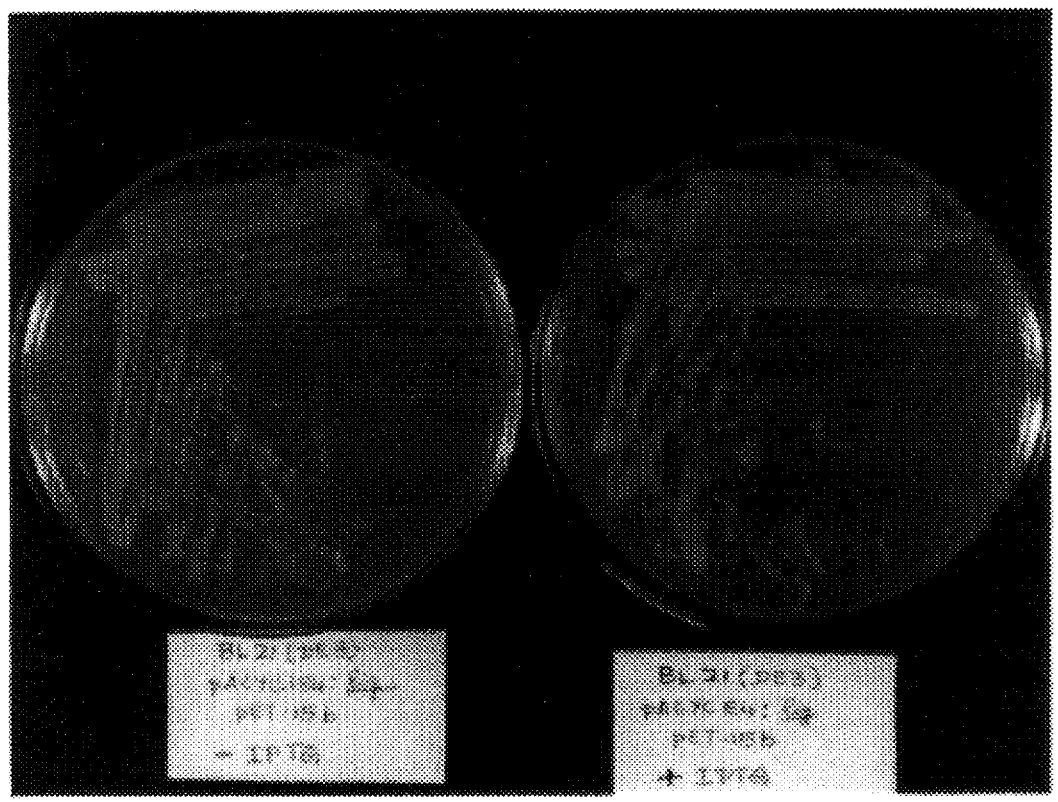
Figure 11B:
Figure 11C:
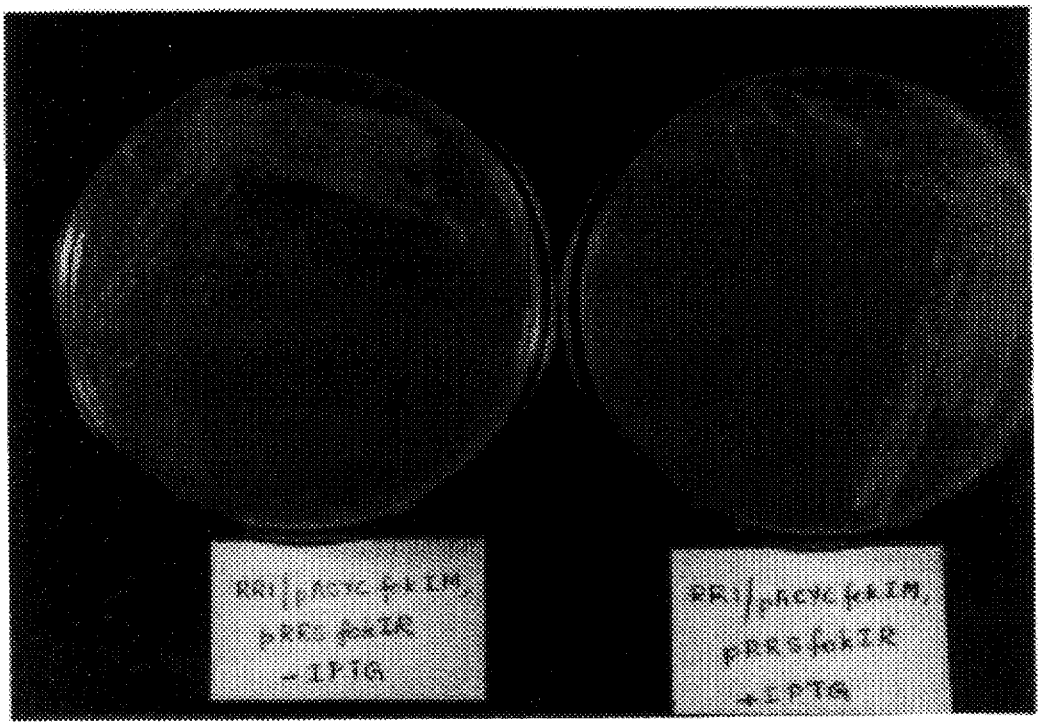

FIGS. 11A–11C show appropriate control cells grown on LB-Amp-Tet plates with and without IPTG. Left, –IPTG and Right, +IPTG. FIG. 11A shows BL21 (DE3) (pACYC lig) (pET-15b). In this clone, pET-15b does not have any insert.

FIG. 11B shows BL21 (DE3) (pACYC lig) (pET-15b:29 kDa). The pET-15b carries a gene encoding a non-lethal 29 kDa fragment cloned downstream of the tac promoter. The protein is inducible by IPTG.

FIG. 11C shows control RRI(pACYC fokIM) (pRRS fokIR). The growth of the control cells are not inhibited by IPTG. All cells grow well in the absence or presence of IPTG.

Figure 12A:
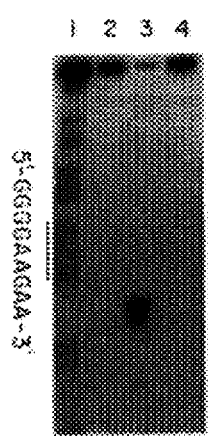
Figure 12B:
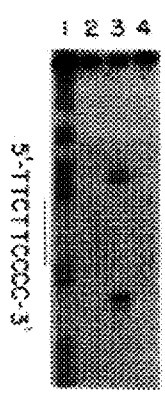

FIGS. 12A–12D show the analyses of the cleavage products of the $^{32}$P-labelled DNA duplexes containing a single binding-site by ZF-F$_N$ fusions. FIGS. 12A and 12B correspond to ZF-QQR-F$_N$ and FIGS. 12C and 12D correspond to ZF-Sp1C-F$_N$. The $^{32}$P-labelled strand of the DNA duplex is indicated on each figure. Lane 1 shows (G+A) sequencing reactions. Lane 2 shows $^{32}$P-labelled substrates. Lane 3 shows ZF-QQR-F$_N$ digestion products and lane 4 shows ZF-Sp1C-F$_N$ digestion products.

ZF-Sp1C-F$_N$ is a specific abbreviation for a fusion product between the three zinc finger motif of the eukaryotic transcription factor Sp1 (a specific zinc finger) and the FokI endonuclease domain (F$_N$).

Figure 12C:
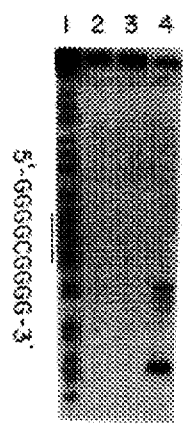
Figure 12D:
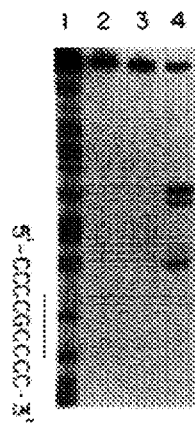
Figure 13:
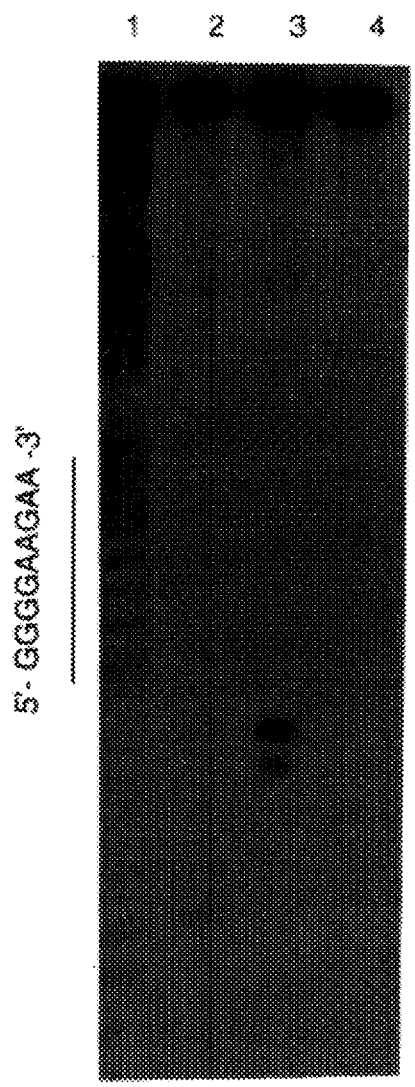

FIG. 13 shows an analysis of the cleavage of a DNA-RNA hybrid by the ZF-QQR-F$_N$ hybrid enzyme. The $^{32}$P-labelled DNA strand also contains the binding site 5'-GGGGAAGAA-3'. The cleavage products were analyzed by PAGE as described for FIG. 12. Lane 1 shows (G+A) sequencing reactions. Lane 2 shows $^{32}$P-labelled DNA-RNA hybrid. Lane 3 shows ZF-QQR-F$_N$ digestion products and lane 4 shows ZF-Sp1C-F$_N$ digestion products.

FIG. 14 shows the map of the recognition and cleavage site(s) of ZF-QQR-F$_N$ hybrid enzyme on DNA (SEQ ID NO:21) and on DNA-RNA hybrid (SEQ ID NO:22 and SEQ ID NO:23) and ZF-Sp1C-F$_N$ hybrid enzyme on DNA (SEQ ID NO:24). The recognition site is shown in bold-faced type and the site(s) of cleavage are indicated by arrows.

Figure 15:
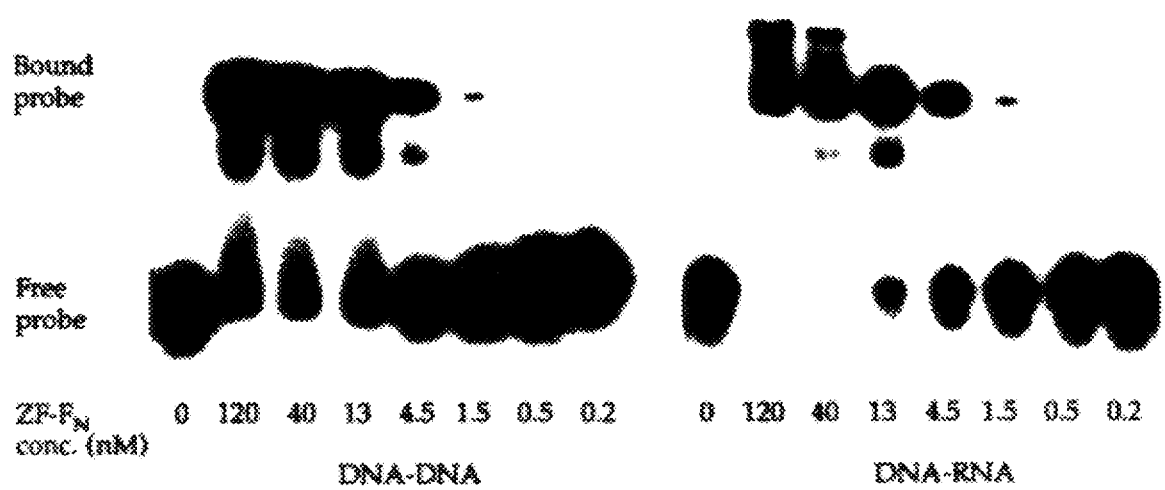

FIG. 15 shows the binding of ZF-QQR-F$_N$ to DNA duplex and DNA-RNA hybrid. The left and right panels show the results of gel shift assays for DNA-DNA and DNA-RNA duplexes, respectively. The conditions for gel mobility-shift experiments were as described by Shi and Berg (34).

DETAILED DESCRIPTION OF THE INVENTION

The present invention discloses a method for cloning hybrid restriction endonucleases and to a method for enzymatically inactivating a target DNA. The latter method involves the use of genes encoding nucleases, including site-specific hybrid restriction endonucleases. The hybrid restriction endonucleases are capable of specifically recognizing, binding to, inactivating and destroying the target DNA. The potential lethality of the hybrid restriction enzymes is initially circumvented by using E. coli DNA lig gene in the former method, i.e., for cloning hybrid restriction endonucleases.

More specifically, the hybrid endonuclease genes are cloned into a tightly controlled expression system to lessen any deleterious effect to the cell and also to increase the level of DNA ligase by placing the E.coli DNA lig gene on a compatible plasmid. This vector expresses the DNA ligase constitutively. Later, in the method for enzymatically inactivating a target DNA, the cells are induced to produce the hybrid restriction endonucleases and to enzymatically inactivate the target DNA.

The methods of the present invention is exemplified by the following non-limiting examples.

EXPERIMENTAL PROCEDURES:

The complete nucleotide sequence of the FokI R-M (restriction-modification) system has been published (21, 22). Experimental protocols for PCR have been described (4). The procedures for cell growth and purification of proteins using His-bind resin (23) was as outlined in the Novagen pET system manual. The protocol for SDS/PAGE was as described by Laemmli (24).

1. Cell Transformation Assay

E. coli strain RR1 and E.coli strain BL21 (DE3) were the host in all experiments. E. coli strain RR1, as reported by Studier et al. (26), and E.coli strain BL21 (DE3), as reported by Maniatis et al. (38), were transformed as described in Maniatis et al. (38). Briefly, the cells were grown to 0.2 OD and incubated with 100 mM CaCl$_2$ for 16 hours at 4° C. to make them competent. These cells were then transfected with DNA as described in Maniatis et al. (38).

2. Construction of the Clones Producing the Hybrid Enzymes ZF-F$_N$ Using PCR

The PCR-generated DNAs using oligos 5'-CCCCTGAAGGAGATATACATATG-3', (SEQ ID NO:25), start primer, and 5'-GGACTAGTCCCTTCTTATTCTGGTG-3', (SEQ ID NO:26), stop primer, were digested with NdeI/SpeI and then ligated into NdeI/SpeI-cleaved pET-15b Ubx-F$_N$ vector which contains the FokI nuclease (F$_N$) domain. This construct replaces the Ubx homeodomain with the genes coding for zinc finger proteins. The ligation mixture was used to transfect competent RR1 (pACYC184:lig) cells. The glycine linker (Gly$_4$Ser)$_3$ (SEQ ID NO:27) was inserted between the zinc finger motifs and the FokI nuclease domain using previously described procedures (16). The zinc finger fusion constructs were confirmed by Sanger's dideoxy sequencing method (25). The pET-15b:ZF-F$_N$ plasmids were then transferred to BL21 (DE3) that carries the compatible plasmid pACYC184:lig.

3. Purification of ZF-F$_N$ Endonucleases

The procedure for the purification of the zinc finger fusion proteins were as follows: 4 L of cells BL21 (DE3) (pACYC184:lig, pET-15:ZF-F$_N$) were grown in LB containing 100 μg/ml of ampicillin and 20 μg/ml of tetracycline at 37° C. When OD$_{600}$ reached 0.4, the growth temperature was shifted to 22° C. The cells were induced at OD$_{600}$=0.5 with 0.7 mM of IPTG. After 4 hrs. of induction at 22° C., the cells were harvested by centrifugation. Induction at 22° C. maximizes the yield of soluble hybrid endonucleases in the crude extracts when compared to induction at 30° C. or 37° C.

The cells were resuspended in Novagen's 1×bind buffer and then disrupted by sonication on ice. After centrifugation at 4° C. for 2 hrs, the crude extract was passed through a 0.45 micron filter and applied to the His-bind affinity column. The column was washed with 1×bind buffer (10 vol.) and 1×wash buffer (6 vol.) as described in Novagen's manual. In addition, the column was washed with 1×wash buffer (4 vol.) containing 100 mM imidazole. The column was eluted with 1×elute buffer containing 400 mM imidazole.

Fractions containing the fusion proteins were identified by probing the immunoblots with rabbit polyclonal antibody against FokI endonuclease. The eluted fractions containing the hybrid proteins were diluted with 3 volumes of buffer A (10 mM Tris base, 15 mM NaH$_2$PO$_4$.H$_2$O, 10% glycerol, 100 μM ZnCl$_2$, 3 mM DTT, pH 8.0) to reduce salt concentration to 125 mM NaCl and then applied to a SP-sepharose column and eluted with a 0.2M–1M linear salt gradient.

Fractions containing the fusion proteins were concentrated using a SP-sepharose column and then loaded onto a S-100 HR gel-filtration column equilibrated with buffer A containing 0.5M NaCl. Following gel-filtration step, pure fractions were combined and the fusion proteins were stored in 50% glycerol at −20° C. or at −70° C. for long-time storage. After the final step of purification, the yield of each purified zinc finger fusion protein was greater than 100 μg per 10 gm of cell paste. The low yield can be attributed to the following: (1) the gene product is toxic to the cells and (2) a large portion of the fusion protein is lost as inclusion bodies.

4. Construction of ZF-ONR Fusions with Different Linkers

The three ZF-QNR-$F_N$ constructs with different linkers were prepared using synthetic oligomers as described below. The inserts for the linkers were made by annealing the appropriate oligomers. These include:

5'-CTGACGGGGGCCAA-3' (SEQ ID NO:28):
3'-TGCCCCCGGTTGATC-5' (SEQ ID NO:29)
for (GlyGly) linker;
5'-CTAGACGGGGGAGGCGGCAGTCAA-3' (SEQ ID NO:30);
3'-TGCCCCCTCCGCCGTCAGTTGATC-5' (SEQ ID NO:31)
for (Gly$_4$Ser) (SEQ ID NO:32) linker; and
5'-CTAGACGGGGGAGGCGGCAGTGGAGGTGGCGGATCACAA-3' (SEQ ID NO:33):
3'-TGCCCCCTCCGCCGTCACCTCCACCGCCTAGTGTTGATC-5' (SEQ ID NO:34)
for (Gly$_4$Ser)2 (SEQ ID NO:35) linker.

The annealed oligonucleotide duplex made from each pair of primers are flanked by SpeI compatible 5'-overhangs at both ends. The oligonucleotide duplexes were phosphorylated by using $T_4$ polynucleotide kinase and ATP. The plasmid pET-15b:ZF-QNR-$F_N$ was digested with SpeI, dephosphorylated using calf intestinal phosphatase and then gel-purified. The phosphorylated inserts were then ligated into the linearized plasmid.

Several clones were screened for the appropriate inserts by restriction enzyme digestion. Plasmid with the right orientation of the inserts were further confirmed by DNA sequencing. The hybrid enzymes with different linkers were partially purified using His-bind affinity column and SP-sepharose column as described above. The DNA cleavage properties of the partially purified proteins were analyzed using the lambda DNA substrate as described above.

EXAMPLES

1. Construction of Overproducer Clones of ZF-$F_N$ Using PCR

Two plasmids containing three zinc fingers each (ZF-QDR and ZF-QNR) were shown to preferentially bind to 5'-G(G/A)G G(C/T/A)G GC(T/A)-3' and 5'-G(G/A)G GA(T/A) GG(G/T)-3' sequences in double-stranded DNA, respectively (13–15). We used the PCR technique to link the zinc finger proteins to the cleavage domain –($F_N$) of FokI endonuclease (FIG. 1A). The hybrid gene, ZF-$F_N$ was cloned as a XhoI/NdeI fragment into pET-15b vector (26), which contains a $T_7$ promoter for expression of the hybrid protein. We also inserted a glycine linker (Gly$_4$Ser)$_3$ (SEQ ID NO:21), between the domains of the fusion protein to confer added flexibility to the linker region (FIG. 1B).

This construct links the zinc finger proteins through the glycine linker to the C-terminal 196-amino acids of FokI that constitute the FokI cleavage domain (8). This construct also tags the hybrid protein with six consecutive histidine residues at the N-terminus. These residues serve as the affinity tag for the purification of the hybrid proteins by metal chelation chromatography (23) with Novagen's His-bind resin. This histidine tag, if necessary, can be subsequently removed by thrombin. The hybrid endonucleases with His tag were used in all experiments described below.

The clones carrying the hybrid genes may not be viable since there is no methylase available to protect the host genome from cleavage by the hybrid endonuclease. We have circumvented this problem as follows: (i) The hybrid genes were cloned into a tightly controlled expression system (26) to avoid any deleterious effect to the cell. (ii) In addition, we increased the level of DNA ligase within the cell by placing the E. coli lig gene on a compatible plasmid pACYC184, downstream of the chloramphenicol promoter. This vector expresses DNA ligase constitutively. BL21 (DE3) served as the host for these experiments. It contains a chromosomal copy of $T_7$ RNA polymerase gene under lacUV5 control, the expression of which is induced by the addition of isopropyl, β-D-thio-galactoside (IPTG).

Figure 2C:
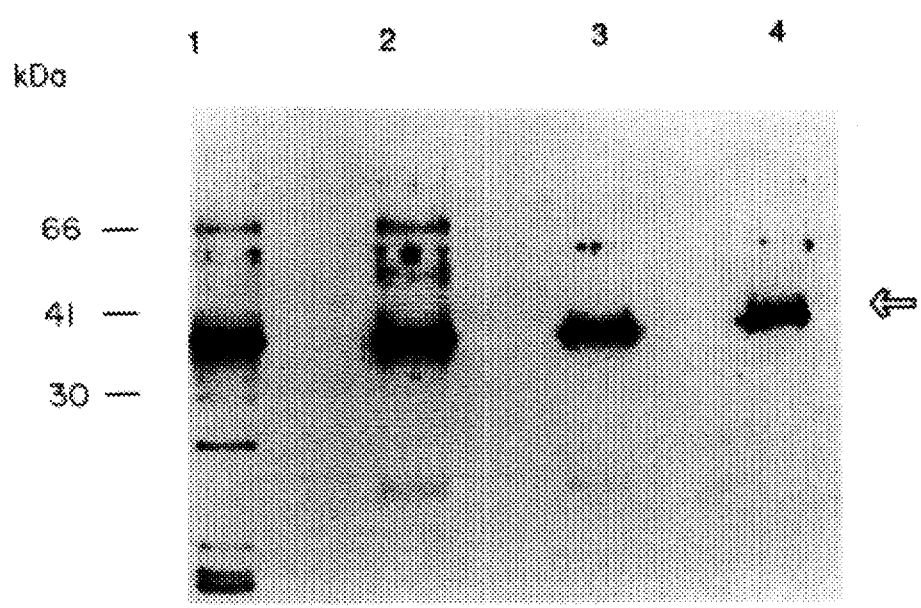
FIG. 2C shows the Western blot profile at each step of purification of ZF-QNR-$F_N$ hybrid enzyme using antisera raised against FokI endonuclease. Lane 1 shows the crude extract from induced cells; lane 2 shows the results of purification after His-bind resin column chromatography; lane 3 shows the results after SP-sepharose column chromatography; and lane 4 shows the results after gel filtration column chromatography. The arrow indicates the intact fusion protein.

After induction of the recombinant cells with 0.7 mM IPTG, the hybrid proteins were purified to homogeneity using His-bind resin, SP-sepharose column and gel filtration chromatography. The SDS/PAGE (25) profiles of the purified hybrid enzymes are shown in FIGS. 2A and 2B. Their size is ~38 kDa and agrees well with that predicted for the fusion proteins. Identities of the hybrid proteins were further confirmed by probing the immunoblot with rabbit antiserum raised against FokI endonuclease (FIG. 2C).

2. Analysis of the Cleavage Activity of the ZF-$F_N$ Hybrid Enzymes

To determine whether the zinc finger fusion proteins cleave DNA, we used 48.5-kb λ DNA as the substrate. The DNA (30 μg/ml; ~10 nM) was incubated with the enzymes (~10 nM) in 35 mM Tris.HCl (pH 8.5), 75 mM KCl, 100 μM ZnCl$_2$, 3 mM DTT containing 5% (v/v) glycerol, 25 μg/ml yeast tRNA and 50 μg/ml BSA for 20 min at room temperature in a total volume of 25 μl. MgCl$_2$ was then added to a final concentration of 2 mM and the mixture incubated at room temperature for 4 more hrs. The reaction products were analyzed by 0.5% agarose gel electrophoresis.

The ZF-QNR-$F_N$ fusion protein cleaves λ DNA into ~9.5 kb and ~39 kb fragments (FIG. 3, lane 4). The cleavage is highly specific and the reaction proceeds almost to completion. The ZF-QDR-$F_N$ fusion protein cleaves λ DNA primarily into a 5.5 kb and a 43 kb fragments (FIG. 3, lane 3). This appears to be the major site of cleavage. There are two other minor sites within the λ genome for this fusion protein. Addition of yeast RNA to the reaction mixture reduces cleavage at the minor site(s). Under these reaction conditions, there was no detectable random nonspecific cleavage as seen from the non-smearing of the agarose gels.

The cleavage is sensitive to buffer conditions, pH and the purity of the DNA substrate. The kinetics of the cleavage of the lambda DNA substrate using ZF-QDR-$F_N$ and ZF-QNR-$F_N$ fusions are shown in the FIG. 4. The cleavage occurs mainly at the major DNA binding site within the lambda genome at short incubation time. The cleavage at the secondary sites become more pronounced with longer incubation times in the case of ZF-QDR-$F_N$ fusion (FIG. 4A).

The cleavage occurs predominantly at the major DNA binding site in the case of the ZF-QNR-$F_N$ fusion. Only a few weaker bands appear even after long incubation times suggesting that there is only one major DNA binding site for ZF-QNR-$F_N$ in the lambda DNA substrate (FIG. 4B).

The reactions appear to proceed almost to completion (>95% cleavage) within 4 hrs. The kinetics of the cleavage of the lambda DNA substrate by wild-type FokI is shown in FIG. 4C. The cleavage reaction by FokI endonuclease proceeds to completion within 15 minutes. The rate and efficiency of cleavage by the hybrid endonucleases are much lower compared to wild-type FokI.

We have also studied the effect of temperature and salt concentrations (KCl and MgCl$_2$) on ZF-QNR-$F_N$ fusion protein cleavage activity using the lambda DNA as a substrate. The results of these experiments are shown in FIG. 5. The cleavage efficiency by ZF-QNR-$F_N$ appears to decrease with increasing temperatures (FIG. 5A). Room temperature (22° C.) appears to be the optimal temperature for the cleavage reaction. This may indicate the decreased binding of the ZF-QNR-F$_N$ fusion protein to the lambda DNA substrate at higher temperatures. The optimal salt concentration for cleavage appears to be 75 mM KCl. Under these conditions, the reaction proceeds to completion (FIG. 5B).

The cleavage efficiency appears to drop off with increasing KCl concentration. This can be attributed to the instability of the protein-DNA complex at higher salt concentrations. The effect of increasing MgCl$_2$ (co-factor) concentration on the cleavage reaction is shown in FIG. 5C. The efficiency of cleavage increases with MgCl$_2$ concentration and the reactions proceed to completion. However, with increasing MgCl$_2$ the nonspecific cleavage by the FokI nuclease domain becomes more pronounced. The optimal MgCl$_2$ concentration for the cleavage reaction appears to be between 2–3 mM.

These experiments demonstrate that cleavage activity of the ZF-QDR-F$_N$ and ZF-QNR-F$_N$ fusions are quite reproducible. Furthermore, they also show that the reaction conditions can be optimized for site-specific cleavage as well as for the complete cleavage of the substrate.

These results are consistent with what is known about zinc finger-DNA interactions. The zinc finger-DNA recognition appears to be by virtue of only two base contacts of the triplet per zinc finger (10). Therefore, zinc fingers may recognize more than one DNA sequence differing by one base in the central triplets. This may explain why the ZF-QDR-F$_N$ hybrid enzyme recognizes several DNA sites with different affinities, and then cuts these sites with different efficiencies. Thus, the subsite bindings of relatively moderate affinity may contribute to the degeneracy of cleavage. On the other hand, the ZF-QNR-F$_N$ fusion suggests that a hybrid restriction enzyme with a high sequence-specificity can be engineered by using the appropriate zinc finger motifs in the fusion constructs.

3. Analysis of the DNA-Sequence Preference of the ZF-F$_N$ Hybrid Enzymes

Determination of the major DNA-binding sites of ZF-QDR-F$_N$ and ZF-QNR-F$_N$ fusion proteins were done in two steps: First, by using a series of known restriction enzyme digests of the λ DNA followed by cleavage with the fusion protein, the site was localized within a 1–2 Kb region of the genome. Second, a 300 bp λ DNA fragment containing the major cleavage site was isolated. This substrate was end-labeled with $^{32}$P on the top DNA strand or the bottom DNA strand. The products of cleavage of each labeled substrate were analyzed by denaturing polyacrylamide gel electrophoresis (25) followed by autoradiography (FIGS. 6A–6B). More specifically, cleavage products of the $^{32}$P-labeled DNA substrate containing a single binding-site by ZF-F$_N$ along with (G+A) sequencing reactions were separated by electrophoresis on a 8% polyacrylamide gel containing 6M urea. The gel was dried and exposed to an x-ray film for 6 hrs.

The map of the primary recognition and cleavage site(s) of the ZF-QDR-F$_N$ and ZF-QNR-F$_N$ fusion proteins found in the λ genome are shown in FIG. 6C and 6D, respectively. The ZF-QDR-F$_N$ fusion protein preferentially binds to 5'-GAG GAG GCT-3', which is one of the four predicted consensus sites that occur in the λ genome. The ZF-QNR-F$_N$ fusion does not bind to any of the four predicted consensus sites that are present in the λ genome. It preferentially binds to the 5'-GAG GGA TGT-3' site that occurs only once in the genome. The two bases that are different from the reported consensus recognition site of ZF-QNR are underlined. The reported consensus DNA binding sites of the zinc finger proteins were determined by affinity-based screening (13–15). This method utilizes a library of DNA binding sites. Under representation of any of the possible sites within this library may lead to the identification of a subsite as the optimal DNA binding site.

Alternatively, the fusion of the zinc finger proteins to the FokI cleavage domain may alter the DNA sequence-specificity. This is unlikely because the binding sites for the previously reported Ubx-F$_N$ and one of the two ZF-F$_N$ fusions described here agree with the reported consensus DNA sites. As many more zinc finger fusions are engineered and characterized, this apparent discrepancy may be resolved. If the sequence-specificity of the hybrids is indeed altered, then we need to develop a fast and efficient screening method to identify or select the DNA binding sites of the hybrid restriction enzymes.

The specificity of the two hybrid restriction enzymes described here are different. More than likely, the specificity of these enzymes are determined solely by the DNA-binding properties of the zinc finger motifs. It appears that the hybrid endonucleases do turnover, that is, the fusion proteins come off the substrate after cleavage. Both enzymes cleave the top strand near the binding site; they cut the bottom strand at two distinct locations. Both fusions show multiple cuts on both strands of the DNA substrate (FIGS. 6A–6D). One possibility is that the cleavage domain is not optimally positioned for cutting. Naturally occurring Type IIS enzymes with multiple cut sites have been reported in the literature (27). The variations in the cleavage pattern of the two hybrid enzymes can be attributed to the differences in the mode of binding of the zinc finger motifs to their respective DNA-binding sites and to the orientation of the nuclease domain within the enzyme-DNA complex.

4. ZF-QNR Fusions with Different Linkers Between the Recognition and Cleavage Domains Five different ZF-QNR-F$_N$ hybrids containing different linkers (Table I) were constructed using synthetic oligomers. The fusion protein from each construct was partially purified using His-bind affinity column and SP-sepharose column. The presence of the fusion proteins were confirmed by Western blots using polyclonal antisera raised against restriction FokI endonuclease. Only small amounts of intact fusion proteins were obtained in the case of the hybrids with (Gly$_4$Ser) (SEQ ID NO:32) and (Gly$_4$Ser)$_2$ (SEQ ID NO:35) linkers and therefore, they were not tested for sequence-specific cleavage activity.

The fusions with no linker, (GlyGly) and (Gly$_4$Ser)$_3$ (SEQ ID NO:27) were partially purified as described above; the hybrid enzymes from constructs with no linker or (GlyGly) linker showed only minimal sequence-specific cleavage (Table I). (Gly$_4$Ser)$_3$ (SEQ ID NO:27) appears to be the optimal spacer between the zinc finger and the FokI cleavage domain. This spacer appears to provide the added flexibility to the two functional domains of the zinc finger hybrids that is necessary for optimal DNA cleavage.

5. Cloning ZF-FN in the Presence of lig Gene

The E.coli lig gene was inserted into the NcoI site of plasmid pACYC184. The plasmid was prepared as described by Chang and Cohen (39) and carries the tetracycline drug marker. The recombinant plasmid carrying the lig gene in the same orientation as the chloramphenicol promoter was identified as pACYC lig (FIG. 7). This recombinant was transfected into competent E.coli strain BL21 (DE3). The hybrid restriction endonuclease genes on a separate compatible plasmid, pET-15b were transfected into competent BL21 (DE3) (pACYC lig) as well as competent BL21(DE3) cells.

0.1 ml of the transformation mix was plated on LB-Amp-Tet plates (FIG. 8). The pTZ19R that does not carry a hybrid endonuclease gene was used as a standard control to compare the efficiency of transformation of the competent cells. BL21 (DE3) (pACYC lig) transformed at about 5–10 fold lower efficiency as compared to the BL21(DE3) cells (FIG. 8).

6. Transformation Efficiency of Hybrid Genes

The transformation efficiency of two different endonuclease genes, pET-15b:ZFHD1-$F_N$ and pET-15b:ZF-QQR-$F_N$, into BL21 (DE3), with and without pACYC lig is summarized in Table II. BL21 (DE3) with pACYC lig transform about 2-fold better compared to BL21 (DE3) without the pACYC lig. Taking into consideration 5–10 fold lower efficiency of BL21 (DE3) (pACYC lig) as compared to BL21 (DE3), this translates into about 10–20 fold difference between E.coli strains with and without pACYC lig.

7. Induction of Hybrid Nuclease Activity

In a different example, pET-15b:ZF-QDR-$F_N$ (where the hybrid endonuclease gene is under the control of a $T_7$ promoter) was transfected into two different E.coli strains, namely RR1 and BL21 (DE3) both without the plasmid, pACYC lig carrying the lig gene. While pET-15b:ZF-QDR-$F_N$ was stably maintained in RR1, it is unstable when it is transfected into BL21 (DE3), which has a copy of the $T_7$ RNA polymerase gene in its chromosome. Only mutants of the hybrid endonuclease gene were obtained upon transfection of competent BL21 (DE3) cells. Plasmids from six different clones were isolated and analyzed by digestion with NdeI/XhoI. While three clones showed that the hybrid restriction endonuclease gene was deleted, the others contained inserts that were 0.9 kb larger than the original gene (FIG. 9). The hybrid gene appears to be disrupted by the insertion of an IS1 element.

We circumvented this problem by transfecting the pET-15:ZF-QDR-$F_N$ into E.coli BL21 (DE3) cells that carry the compatible plasmid (pACYC lig) which has the E.coli lig gene inserted downstream of the chloramphenicol promoter. This plasmid expresses the DNA ligase constitutively. The pET-15b:ZF-QDR-$F_N$ is stable within these cells. Induction of these clones with IPTG result in the production of the hybrid enzyme. This is an important finding and development since this implies that any hybrid endonuclease will be tolerated by the cells provided they can express the DNA ligase constitutively and thereby repair the damage. No methylase is needed to protect the host genome from cleavage by the hybrid endonuclease.

We have cloned several hybrid endonucleases using this approach. This is summarized in Table III. ZF-Sp1C-$F_N$ is a specific abbreviation for a fusion product between the three zinc finger motif of the eukaryotic transcription factor Sp1 (a specific zinc finger) and the FokI endonuclease domain ($F_N$).

This patent application is for a method of cloning any hybrid endonuclease gene in any type of cell wherein any DNA ligase is produced at an increased level compared to the normal level of DNA ligase in the specific cell type. More specifically, the method of this patent application includes the cloning of any hybrid endonuclease gene in any prokaryotic (e.g., E. coli, mutants of E. coli, etc.) or eukaryotic (e.g., yeast, plant or mammalian, etc.) cell that has been altered to produce increased levels of any type of DNA ligase (e.g., $T_4$ ligase gene, etc.) within the cell.

8. Induction of Anti-Bacterial Activity with Hybrid Nuclease

A specific application for these engineered sequence-specific endonucleases is in the cleavage, and thereby inactivation of genes in vivo. Several methods are currently available to express foreign genes in a number of bacterial, fungal, plant and animal species. These include transient expression via episomal or viral vectors or by microinjection. Such methods could be used for the delivery and expression of hybrid endonucleases within cells. Essentially any DNA intermediate is a potential target or substrate for cleavage by a hybrid endonuclease. These include RNA tumor viruses which replicate through a DNA intermediate. It should be possible to target one or more hybrid endonucleases against these specific DNA intermediates provided the gene sequences are known. Expression in vivo of such hybrid restriction enzymes would in effect destroy the corresponding gene. This targeted gene inactivation by the hybrid endonucleases could provide a basis for various anti-viral and anti-bacterial therapies and for a way to inactivate human, animal or plant genes.

In another example, plasmids containing one of two different hybrid endonucleases, namely pET-15b:ZF-QDR-$F_N$ and pET-15b:ZF-QNR-$F_N$, were separately transfected into E.coli BL21 (DE3) (pACYC lig) by standard $CaCl_2$ procedure. The clones were then plated on LB-Amp-Tet plates with and without IPTG. Induction with IPTG turns on the production of $T_7$ RNA polymerase, which lead to the production of the hybrid restriction enzymes. The constitutively produced ligase cannot cope and repair the damage resulting from the hybrid restriction enzymes. Therefore, the clones should not be viable upon induction with IPTG.

FIGS. 10A and 10B show the results obtained from such an experiment. BL21 (DE3) (pACYC lig) containing the hybrid endonuclease genes on a compatible plasmid grow well on LB-Amp-Tet plates without IPTG. No growth is observed when they are grown on LB-Amp-Tet plates containing 1 mM IPTG. Control BL21 (DE3) (pACYC lig) (pET-15b) strain that does not carry the hybrid restriction endonuclease gene grow well on LB-Amp-Tet plates with and without IPTG (FIG. 11).

This example shows that bacteria carrying the hybrid restriction enzymes gene can be forced to self-destruct by inducing the hybrid restriction enzymes. This example also provides proof of concept for potential use of hybrid restriction enzymes as therapeutic agents. Obviously, the hybrid restriction endonuclease genes could also be delivered into cells via a plasmid, virus, phage or any other delivery vehicle that infects a particular type of bacterial or mammalian cells, including plant and animal cells.

Bacteriophages have been shown to be effective in the treatment of experimental E.coli infection (10,11). More recently, bacteriophage was shown to prevent destruction of skin grafts by Pseudomonas aeruginosa (12). These bacteriophages can be engineered to carry the lethal hybrid endonuclease genes targeted against their hosts. These bacteriophages will be more effective in the destruction of the bacteria they infect. The present invention specifically includes this concept as well. The present invention also contemplates the delivery of other normal as well as mutant site-specific restriction enzymes using a similar approach.

9. Site-Specific Cleavage of DNA-RNA Hybrids

As mentioned above, zinc finger proteins of the type $Cys_2His_2$ are quite prevalent in human and other eukaryotic genomes (33). Recently, two such proteins, ZF-SP1C and ZF-QQR, were shown to bind DNA-RNA hybrids with affinities comparable to those of DNA duplexes (34). We have converted these specific zinc finger proteins into site-specific endonucleases by linking them to the FokI cleavage domain ($F_N$), as described above. Here, we show that the ZF-QQR-F$_N$ fusion enzyme binds to and cleaves DNA-RNA hybrids in a sequence-dependent manner.

Crystal structures of zinc finger protein-DNA complexes (10–12) have shown that the proteins contact one strand of the DNA much more than the other strand. The three-zinc finger binding unit from the transcription factor Sp1 (ZF-Sp1C) was shown to bind a 19-base pair DNA fragment containing the site 5'-GGGGCGGGG-3' with a similar affinity to that of DNA-RNA hybrid with the DNA strand containing this guanine-rich site (34). Furthermore, a designed consensus sequence-based protein (14), ZF-QQR was shown to bind DNA-RNA hybrid containing the site 5'-GGGGAAGAA-3' on the DNA strand about five times as tightly as the DNA duplex. We reasoned that by linking these zinc finger proteins to the FokI cleavage domain, it might be possible to engineer site-specific endonucleases that cleave DNA-RNA hybrids. PCR technology was used to link the zinc finger proteins to the cleavage domain of FokI to generate the hybrid genes, ZF-QQR-FP and ZF-SP1C-F$_N$, respectively, as described above. This construction links the zinc finger proteins through a glycine linker to the C-terminal 196-amino acids of FokI endonuclease that constitutes the FokI cleavage domain (4,8).

The cleavage properties of the purified ZF-F$_N$ fusions were analyzed using $^{32}$P-labelled DNA substrates each containing a single binding site. The plasmid pBluescript KS(+) containing the ZF-QQR site was digested with KpnI (or SacI), then dephosphorylated using calf intestinal phosphatase (CIP) and rephosphorylated using T$_4$ polynucleotide kinase and γ-$^{32}$P-ATP. The DNA was digested with SacI (or KpnI) and the small fragment with the $^{32}$P label on the top strand (or the bottom strand) was purified by gel electrophoresis.

The restriction enzymes BamHI (or EcoRI) were used to cleave pBluescript KS(+) containing the ZF-Sp1C site to prepare $^{32}$P labelled substrates. The $^{32}$P labelled substrates with 300 ng of cold DNA (tRNA or lambda DNA) in 35 mM Tris.HCl (pH 7.5), 75 mM KCl, 100 µM ZnCl$_2$, 5 mM DTT, 0.5 µg BSA and 5% glycerol were incubated with ZF-F$_N$ fusions for 30 minutes at room temperature. MgCl$_2$ was then added to a final concentration of 2 mM and digested for 5 hours. The products from the reaction mixture were then analyzed by PAGE. The cleavage products along with (G+A) sequencing reaction (36) were separated by electrophoresis on an 8% polyacrylamide gel containing 6M urea. The gel was dried and then exposed to an x-ray film for 6 hours.

ZF-Sp1C-F$_N$ binds to 5'-GGGGCGGGG-3' and cleaves 5' to this site on both strands of the DNA duplex (FIGS. 12C and 12D). ZF-QQR-F$_N$ binds to the 5'-GGGGAAGAA-3' site and cleaves upstream of this site on both strands of the DNA substrate (FIGS. 12A and 12B). Cleavage is also observed 3' to the site. This is likely associated with binding to a secondary site. This part of the example indicates that both fusion proteins bind to their appropriate binding sites within the substrate and, as expected, cleave upstream of their respective binding sites.

To examine the specificity and cleavage of the DNA-RNA hybrids, analogous $^{32}$P-labelled substrate with the DNA strand containing 5'-GGGGAAGAA-3'site was digested with ZF-QQR-F$_N$. The results from this part of the example are shown in FIG. 13.

The $^{32}$P-labelled DNA-RNA hybrid was prepared as follows: The DNA was chemically synthesized and purified. The oligonucleotide was the phosphorylated using T$_4$ polynucleotide kinase and γ-$^{32}$P-ATP. The RNA strand was then transcribed using T$_3$ RNA polymerase. The RNA-DNA hybrid was digested with ZF-QQR-F$_N$ fusion enzyme as described for FIG. 12 and then analyzed by PAGE.

ZF-QQR-F$_N$ binds to the 5'-GGGGAAGAA-3'site and cleaves 5' to the binding site on the DNA strand of the DNA-RNA hybrid (FIG. 13, lane 3). However, the cut site(s) is shifted one base closer to the binding site compared to the DNA duplex cleavage. This may be attributed to the fact that DNA-RNA hybrids probably have structures distorted away from the B-form due to the presence of 2' hydroxyl groups in the RNA strand. ZF-Sp1C-F$_N$ does not bind to and cleave the DNA-RNA hybrid which contains the 5'-GGGGAAGAA-3' site that is specific for ZF-QQR-F$_N$ (FIG. 13, lane 4). In addition, only minor cleavage was observed 3' to the 5'-GGGGAAGAA-3' binding site unlike that of the DNA duplex. ZF-QQR-F$_N$ appears to preferentially contact the DNA strand of the DNA-RNA hybrid. The complementary RNA strand greatly reduces the secondary site binding of ZF-QQR-F$_N$.

In another part of this example, 32P-labelled substrate with the DNA strand containing the 5'-GGGGCGGGG-3' site was digested with ZF-Sp1C-F$_N$ fusion enzyme. The cleavage of the DNA strand of the DNA-RNA hybrid was not detectable. This result is consistent with the dissociation constants (kd) reported for ZF-Sp1C (40 nM) compared to ZF-QQR (2.8 nM) binding to DNA-RNA hybrids (34). As expected, the cleavage of the RNA-DNA hybrid by ZF-Sp1C-F$_N$ is about 15–20 fold lower than that of ZF-QQR-F$_N$. The cleavage properties of ZF-F$_N$ fusion enzymes are summarized in FIG. 14.

To compare the efficiency of cleavage of the DNA-RNA hybrid and the DNA-DNA duplex, both $^{32}$P-labelled substrates were digested with ZF-QQR-F$_N$ in the same reaction tube. While the cleavage of the DNA duplex proceeded to completion within 4 hours, only about 1% of the DNA-RNA hybrid was cleaved during this time. Thus, the site-specific cleavage of the DNA-RNA hybrid occurs at a much lower rate (~100 fold) compared to that of the DNA duplex.

One possible explanation for the lower rate of the cleavage of the DNA-RNA hybrid may be that the fusion of the ZF-QQR protein to the FokI cleavage domain alters its binding affinity for the substrate. Alternatively, the FokI cleavage domain probably has evolved to cleave only the DNA strand. To delineate between these two possibilities, we determined the apparent dissociation constant of ZF-QQR-F$_N$ binding to DNA-RNA hybrid by using gel mobility-shift assays (FIG. 15). We obtained an apparent dissociation constant of ~3 nM similar to the one reported for ZF-QQR (2.8 nM). Thus, ZF-QQR fusion to the FokI cleavage domain does not alter its sequence-specificity or its substrate affinity. Therefore, it appears that the FokI cleavage domain has evolved to restrict only DNA strands and not RNA strands.

To further examine the cleavage of the RNA strand, a DNA-RNA hybrid with the DNA strand containing the binding site 5'-GGGGAAGAA-3' and the $^{32}$P-label on the RNA strand was digested with ZF-QQR-F$_N$ fusion enzyme. No detectable cleavage of the RNA strand by ZF-QQR-F$_N$ fusion enzyme was observed. Zinc finger fusions that cleave RNA strands may be developed by the fusion of zinc finger proteins to various RNA cleaving moieties. Alternatively, in vitro molecular evolution methods could be adopted to identify enzymes that will cleave the RNA strand.

In summary, this example shows that an engineered zinc finger fusion enzyme, ZF-QQR-F$_N$, can cleave RNA-DNA hybrids in a sequence-dependent manner. Thus, these fusion enzymes may have further important biological applications. Essentially any DNA-RNA intermediate is a potential substrate for cleavage by these zinc finger fusion enzymes. These include RNA tumor viruses which replicate through a DNA intermediate. It should be possible to target one or more of these hybrid endonucleases against these specific DNA-RNA intermediates provided that the gene sequences are known and that the zinc finger proteins that bind to these sequences are available. Expression in vivo of such hybrid restriction enzymes would in effect destroy the corresponding gene. This targeted gene inactivation by the hybrid endonucleases could provide a basis for various anti-viral therapies.

The following scientific article have been cited throughout the present application and are hereby incorporated by reference in their entirety and relied upon:

1. Smith H. O. & Wilcox, K W., *J. Mol. Biol.* 51: 379–391, 1970.
2. Wilson, G. G., *The NEB Transcript* 5: 1, 1993.
3. Roberts, R., *The NEB Transcript* 5: 13, 1993.
4. Li, L., Wu, L. P. & Chandrasegaran, S., *Proc. Natl. Acad. Sci U.S.A.* 89: 4279–4275, 1992.
5. Li, L., Wu, L. P., Clark R. & Chandrasegaran, S., *Gene* 133: 79–84, 1993.
6. Li, L. & Chandrasegaran, S., *Proc. Natl. Acad. Sci U.S.A.* 90: 2764–2768, 1993.
7. Kim, Y.-G., Li, L. & Chandrasegaran, S., *J. Biol. Chem.* 269: 31978–31982, 1994.
8. Kim, Y.-G. & Chandrasegaran, S., *Proc. Natl. Acad. Sci. U.S.A.* 91: 883–887, 1994.
9. Berg, J. M., *Proc. Natl. Acad. Sci. U.S.A.* 85: 99–102, 1988.
10. Pavietich, N. P. & Pabo, C. O., *Science* 252: 809–817, 1992.
11. Pavietich, N. P. & Pabo, C. O., *Science* 261: 1701–1707, 1993.
12. Fairall, L., Schwabe, J. W. R., Chapman, L., Finch, J. T. & Rhodes, *Nature (London)* 366: 483–487, 1993.
13. Desjarlais, J. R. & Berg, J. M., *Proc. Natl. Acad. Sci. U.S.A.* 89: 7345 7349, 1992.
14. Desjarlais, J. R. & Berg, J. M., *Proc. Natl. Acad. Sci U.S.A.* 90: 2256–2260, 1993.
15. Desjarlais, J. R. & Berg, J. M., *Proc. Natl. Acad. Sci U.S.A.* 91: 11099–11103, 1994.
16. Rebar, E. J. & Pabo, C. O., *Science* 263: 671–673, 1994.
17. Choo, Y. & Klug, A., *Proc. Natl. Acad. Sci. U.S.A.* 91: 11163–11167, 1994.
18. Choo, Y. & Klug, A., *Proc. Natl. Acad. Sci. U.S.A.* 91: 11168–11172, 1994.
19. Jamieson, A. C., Kim, S.-H. & Wells, J. A., *Biochemistry* 33: 5689–5695, 1994.
20. Wu, H., Yang, W.-P. & Barbas III, C. F., *Proc. Natl. Acad. Sci. U.S.A.* 92: 344–348, 1995.
21. Kita, K., Kotani, H., Sugisaki H. & Takanami, M., *J. Biol. Chem.* 264: 5751–5756, 1989.
22. Looney, M. C., Moran, L. S., Jack, W. E., Feehery, G. R., Benner, J. S., Slatko, B. E. & Wilson, G. G., *Gene* 80: 193–208, 1989.
23. Hochuli, E., Dobeli, H. & Schacher, A., *J. Chromatogr.* 411: 177–184, 1987.
24. Laemili, U. K., *Nature* (London) 222: 680–685, 1970.
25. Sanger, F., Nicklen S. & Coulson, A. R., *Proc. Natl. Acad. Sci. U.S.A.* 74: 5463–5467, 1977.
26. Studier, F. W., Rosenberg, A. H., Dunn J. J. & Dubendorff, J. W., *Methods in Enzymol.* 185: 60–89, 1990.
27. Szybalski, W., Kim, S. C. Hasan, N. & Podhajska, A. J., *Gene* 100: 13–26, 1991.
28. Waugh, D. S. and Sauer, R. T., *Proc. Natl. Acad. Sci. U.S.A.* 90: 9596–9600, 1993.
29. Waugh, D. S. and Sauer, R. T., *J. Biol. Chem.* 269: 12298–12303, 1994.
30. Smith, W. H. & Huggins, M. B., *J. Gen. Microbiol.* 128: 307–318, 1982.
31. Smith, W. H., Huggins, M. B. & Shaw, K. M., *J. Gen Microbiol.* 133: 1111–1126, 1987.
32. Soothill, J. S., Burns 20: 209–211, 1994.
33. Rhodes, D. & Klug, A., *Sci. Am.* 268: 56–59, 1993.
34. Shi, Y. & Berg, J. M., *Science* 268: 282–284, 1995.
35. Hochuli, E., Dobeli, H. & Schacher, A., *J. Chromatogr.* 411: 177–184, 1987.
36. Maxam, A. M. & Gilbert, W., *Proc. Natl. Acad. Aci. U.S.A.* 74: 560–564, 1977.
37. Birkenbihl, R. P. & Vielmetter, W., *Mol. Gen. Genet.* 220: 147–153, 1989.
38. Maniatis, T., Fritsch, E. F. and Sambrook, J., *Molecular Cloning, A Laboratory Manual*, Cold Spring Harbor Laboratory, New York, 1982.
39. Chang A. C. Y. & Cohen, S. N., *J. Bacteriol.* 134: 1141–1156, 1978.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims.

TABLE I

| Zif-ONR fusions with | | |
|---|---|---|
| Linker | Expression[1] | Activity (specific)[2] |
| No Linker | + | + |
| GG | + | + |
| $G_4S$ (SEQ ID NO: 32) | − | n.t. |
| $(G_4S)_2$ (SEQ ID NO: 35) | − | n.t. |
| $(G_4S)_3$ (SEQ ID NO: 27) | ++ | +++ |

[1]The fusion protein from each construct was partially purified using His-bind affinity column and SP-sepharose column. The expression of the fusions were confirmed by Western blot using polyclonal antisera raised against FokI.
[2]Sequence-specific cleavage was assayed using lambda DNA as substrate.
n.t., Not tested.

TABLE III

Comparison of the Efficiency of transformation of the hybrid endonuclease genes in *E. coli* with and without pACYC lig

| BL21 (DE3) | pACYC lig | Plate #1 | Plate #2 | Average | Ratio[1] |
|---|---|---|---|---|---|
| pET-15b:ZFHD1-FN | − | 135 | 111 | 123 | |
| pET-15b:ZFHD1-$F_N$ | + | 309 | 292 | 300 | ~2.4 |
| pET-15b:ZF-QQR-$F_N$ | − | 375 | 500 | 437 | |
| pET-15b:ZF-QQR-$F_N$ | + | 850 | 1153 | 1001 | ~2.3 |

[1]Taking into consideration 5–10 fold lower transformation efficiency of BL21 (DE3) (pACYC lig) competent cells as compared to BL21 (DE3), this translates into about 0–20 fold difference between *E. coli* strains with and without pACYC lig.

TABLE III

Summary of hybrid endonucleases cloned using *E. coli* DNA lig gene.

| Fusion Protein | Linker | Sequence-Specific-Activity | Predicted Cleavage Sites | Identified Cleavage Site |
|---|---|---|---|---|
| ZF-QNR-$F_N$ | (SEQ ID NO: 27) ($G_4S)_3$ | + | 5'-G$^G_A$ G$^T_A$ GA G$^G_A$ G$^G_T$ -3' | 5'-GAG GGA TGT-3' |
| ZF-QDR-$F_N$ | ($G_4S)_3$ | + | 5'-G$^G_A$ G$^C_T_A$ G$^T_A$ GC -3' | 5'-GAG GAG GCT-3' |
| ZF-QQR-$F_N$ | ($G_4S)_3$ | + | 5'-G$^G_A$ G$^G_T$ $^T_A$ $^G_T$ $^T_A$ -3' | 5'-GGG GAA GAA-3' |
| ZF-SP1C-$F_N$ | ($G_4S)_3$ | + | 5'-G$^G_A$ G$^C_T_A$ G$^T_A$ GG$^G_T$ -3' | 5'-GGG GCG GGG-3' |

What is claimed is:

1. A method for producing a nuclease in a cell wherein said nuclease, when produced in a cell comprising a target nucleic acid which comprises a target nucleotide sequence specifically binds to said target nucleotide sequence and cleaves said target nucleic acid specifically bound to said nuclease,
said method comprising the steps of:

a) providing a preparation of a first polynucleotide encoding said nuclease, wherein said preparation does not comprise a second polynucleotide encoding an enzyme which protects said target nucleic acid from said nuclease by specifically binding to said target nucleotide sequence and enzymatically modifying said target nucleic acid such that said target nucleic acid is not cleaved by said nuclease; and b) delivering said preparation of said first polynucleotide encoding said nuclease into said cell under conditions such that said first polynucleotide expresses said nuclease, thereby producing said nuclease.

2. The method of claim 1, wherein said polynucleotide encoding said nuclease is delivered into said cell by liposomes.

3. The method of claim 1, wherein said delivering step further comprises integrating said first polynucleotide encoding said nuclease into a chromosome of said cell.

4. The method of claim 1, wherein said polynucleotide encoding said nuclease further comprises control elements.

5. The method of claim 1, wherein said cell is a prokaryotic cell.

6. The method of claim 5, wherein said cell is an $E.\ coli$ cell.

7. The method of claim 1, wherein said cell is a eukaryotic cell.

8. The method of claim 7, wherein said cell is a plant cell.

9. The method of claim 7, wherein said cell is a mammalian cell.

10. The method of claim 1, wherein said nuclease is a naturally occurring restriction endonuclease.

11. The method of claim 1, wherein said nuclease is a non-naturally occurring enzyme.

12. The method of claim 11, wherein said nuclease comprises a recognition domain which specifically binds to said target sequence and a separate catalytic domain which cleaves nucleotide sequences non-specifically and is obtained from a nuclease not comprising said recognition domain.

13. A method according to claim 12 wherein said catalytic domain is obtained from the FokI restriction endonuclease.

14. A method according to claim 12 wherein said recognition domain comprises a zinc finger domain.

15. The method of claim 14, wherein said nuclease is selected from the group consisting of ZF-QDR-$F_N$, ZF-Sp1C-$F_N$, ZF-QNR-$F_N$, ZF-QQR-$F_N$ and ZFHD1-$F_N$.

16. A method of claim 1 wherein said cell in which said nuclease is to be produced comprises said target nucleic acid and said target nucleic acid is to be specifically inactivated, wherein further said nuclease produced in said cell specifically inactivates said target nucleic acid by specifically binding to said target nucleotide sequence and cleaving said target nucleic acid bound to said nuclease.

17. The method of claim 16, wherein said target nucleic acid is exogenous to said cell.

18. The method of claim 17, wherein said target nucleic acid is a self-replicating DNA, linear or circular.

19. The method of claim 17, wherein said target nucleic acid is a replication intermediate of an RNA tumor virus.

20. The method of claim 16, wherein said target nucleic acid is a DNA endogenous to said cell.

21. The method of claim 20, wherein said target nucleic acid is chromosomal DNA of said cell.

22. A method according to claim 1 wherein said target nucleic acid is a DNA:RNA hybrid.

23. A method according to claim 1 wherein said target nucleotide sequence comprises a sequence of more than 6 nucleotides.

24. A method according to claim 23 wherein said target nucleotide sequence comprises a sequence of more than 8 nucleotides.

25. A method of claim 1 wherein said cell in which said nuclease is to be produced is to be cloned, and said cell comprises said target nucleic acid and said target nucleic acid is required for cloning of said cell, said method further comprising the steps of:

c) providing a third polynucleotide encoding a DNA ligase; and d) delivering said third polynucleotide to said cell before or concurrently with said step of delivering said preparation of said first polynucleotide into said cell, under conditions such that said DNA ligase is produced whereby said target nucleic acid is protected by said DNA ligase from inactivation by said nuclease produced in said cell; and e) cloning said cell producing said nuclease and said ligase.

26. The method of claim 25, wherein said cell is a prokaryotic cell.

27. The method of claim 26, wherein said cell is an $E.\ coli$ cell.

28. The method of claim 25, wherein said is a eukaryotic cell.

29. The method of claim 28, wherein said cell is a plant cell.

30. The method of claim 28, wherein said cell is a mammalian cell.

31. The method of claim 25, wherein said cell is a mutant or engineered strain that produces an increased level of DNA ligase.

32. The method of claim 25, wherein said nuclease is selected from the group consisting of ZF-QDR-$F_N$, ZF-SP1C-$F_N$, ZF-QNR-$F_N$, ZF-QQR-$F_N$ and ZFHD1-$F_N$.

* * * * *

UNITED STATES PATENT AND TRADEMARK OFFICE
CERTIFICATE OF CORRECTION

PATENT NO.      : 5,792,640

DATED           : December 8, 1997

INVENTOR(S)     : CHANDRASEGARAN, Srinivasan

It is certified that error appears in the above-identified patent and that said Letters Patent is hereby corrected as shown below:

Page 1, line [22], change "Dec. 24, 1995" to --Dec. 20, 1995--.

Signed and Sealed this

Ninth Day of February, 1999

Attest:

Attesting Officer

*Acting Commissioner of Patents and Trademarks*

(12) EX PARTE REEXAMINATION CERTIFICATE (6425th)
United States Patent
Chandrasegaran

(10) Number: US 5,792,640 C1
(45) Certificate Issued: Sep. 9, 2008

(54) GENERAL METHOD TO CLONE HYBRID RESTRICTION ENDONUCLEASES USING LIG GENE

(75) Inventor: Srinivasan Chandrasegaran, Baltimore, MD (US)

(73) Assignee: The National Institutes of Health, Bethesda, MD (US)

Reexamination Request:
No. 90/008,524, Mar. 12, 2007

Reexamination Certificate for:
Patent No.: 5,792,640
Issued: Aug. 11, 1998
Appl. No.: 08/575,361
Filed: Dec. 20, 1995

Certificate of Correction issued Feb. 9, 1999.

Related U.S. Application Data

(63) Continuation-in-part of application No. 08/346,293, filed on Nov. 23, 1994, now Pat. No. 5,487,994, which is a continuation-in-part of application No. 08/126,564, filed on Sep. 27, 1993, now Pat. No. 5,436,150, which is a continuation-in-part of application No. 08/017,493, filed on Feb. 12, 1993, now abandoned, which is a continuation-in-part of application No. 07/862,831, filed on Apr. 3, 1992, now Pat. No. 5,356,802.

(51) Int. Cl.
*C12N 9/22* (2006.01)
*C12Q 1/68* (2006.01)

(52) U.S. Cl. .................................. 435/199; 435/91.1
(58) Field of Classification Search .................. None
See application file for complete search history.

(56) References Cited

PUBLICATIONS

Guhan, N., et al., "Structural and Functional Characteristics of Homing Endonucleases," Critical Reviews in Biochemistry and Molecular Biology, 38(3): 199–248, 2003.
Choulika, A., et al., "Induction of Homologous Recombination in Mammalian Chromosomes by Using the I–SecI System of Sacharomyces cerevisiae," Molecular and Cellular Biology, Apr. 1995, pp. 1968–1973.
Dujon, B., "Group I Introns as Mobile Genetic Elements: Facts and Mechansitic Speculation—a Review," Gene, 82, 1989, pp. 91–114.
Lewin, B., "Perpetuation of DNA," Genes, Third Edition, pp. 336–339, 1987.
Kim, Y.G., et al., "Chimeric Restriction Endonuclease," Proc. Natl. Acad. Sci. USA, vol. 91, pp. 883–887, Feb. 1994.
Li, L., et al., "Functional Domains in Fok I Restriction Endonuclease," Proc. Natl. Acad. Sci. USA, vol. 89, pp. 4275–4279, May 1992.

Colleaux, L., et al., "Universal Code Equivalent of a Yeast Mitochondrial Intron Reading Frame is Expressed into *E. coli* as a Specific Double Strand Endonuclease," Cell, vol. 44, pp. 521–533, Feb. 28, 1986.
Morgan, W. F., et al., "Inducible Expression and Cytogenetic Effects of the EcoRI Restriction Endonuclease in Chinese Hamster Ovary Cells," Molecular and Cellular Biology, pp. 4204–4211, Oct. 1988.
Li, L., et al., "Alteration of the Cleavage Distance of Fok I Restriction Endonuclease by Insertion Mutagenesis," Proc. Natl. Acad. Sci USA, vol. 90, p. 2764–2768, Apr. 1993.
Puchta, H., et al., "Homologous Recombination in Plant Cells is Enhanced by In Vivo Induction of Double Strand Breaks into DNA by a Site–Specific Endonuclease," Nucleic Acids Research, vol. 21, No. 22, pp. 5034–5040, 1993.
Oelgeschläger, T., et al., "Probing the Function of Individual Amino Acid Residues in the DNA Binding Site of the EcoRI Restriction Endonuclease by Analysing the Toxicity of Genetically Engineered Mutants," Gene, 89, pp. 19–27, 1990.
Panayotatos, N., et al., "A Site–Targeted Recombinant Nuclease Probe of DNA Structure," The Journal of Biological Chemistry, Bol. 264, No. 25, pp. 15070–15073, Sep. 5, 1989.
Panayotatos, No., et al., "Biosynthesis of a Repressor/Nuclease Hybrid Protein," The Journal of Biological Chemistry, Bol. 264, No. 25, 15066–15069, Sep. 5, 1989.
Sadler, J. R., et al., "A Perfectly Symmetric Las Operator Binds the Lac Repressor Very Tightly," PNAS, 80, 6785–6789, 1983.
Rudin, N., et al., Efficient Repair of HO–Induced Chromosomal Breaks in Saccharomyces cerevisiae by Recombination Between Flanking Homologous Sequences, Molecular and Cellular Biology, pp. 3918–3928, Sep. 1988.
Rudin, N., et al., "Genetic and Physical Analysis of Double–Strand Break Repair and Recombination in Saccharomyces cerevisiae," Genetics, 122, Jul. 1989, pp. 519–534.

*Primary Examiner*—Bennett Celsa

(57) ABSTRACT

The present invention reveals methods for cloning hybrid restriction endonucleases and for enzymatically inactivating a target DNA. The method for cloning hybrid restriction endonucleases involves co-expression of a ligase. A first plasmid contains a gene encoding a DNA ligase. A second plasmid contains a gene encoding a hybrid restriction endonuclease and is compatible with the first plasmid. The method involves transfecting host cells with the first plasmid, so that DNA ligase is produced, followed by transfecting the cells with the second plasmid. The method for enzymatically inactivating a target DNA involves preparing a plasmid, phage, virus or any other delivery vehicle such as a liposome containing a gene encoding a nuclease, delivering the gene into cells, inducing the cells to produce the nuclease and enzymatically inactivating the target DNA.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5–7 and 10–11 are cancelled.

Claims 1, 8, 9 and 12 are determined to be patentable as amended.

Claims 3–4, 8–9, 13–14, 16–21 and 23–24, dependent on an amended claim, are determined to be patentable.

New claims 33–43 are added and determined to be patentable.

Claims 2, 15, 22 and 25–32 were not reexamined.

1. A method for producing a *non-naturally occurring* nuclease in a *eukaryotic* cell wherein said *non-naturally occurring* nuclease, when produced in a *eukaryotic* cell comprising a target nucleic acid which comprises a target nucleotide sequence specifically binds to said target nucleotide sequence and cleaves said target nucleic acid specifically bound to said nuclease, said method comprising the steps of:
a) providing a preparation of a first polynucleotide encoding said *non-naturally occurring* nuclease, wherein said preparation does not comprise a second polynucleotide encoding an enzyme which protects said target nucleic acid from said nuclease by specifically binding to said target nucleotide sequence and enzymatically modifying said target nucleic acid such that said target nucleic acid is not cleaved by said nuclease; and
b) delivering said preparation of said first polynucleotide encoding said *non-naturally occurring* nuclease into said *eukaryotic* cell under conditions such that said first polynucleotide expresses said *non-naturally occurring* nuclease, thereby producing said *non-naturally occurring* nuclease.

8. The method of claim [7] *1*, wherein said cell is a plant cell.

9. The method of claim [7] *1*, wherein said cell is a mammalian cell.

12. The method of claim [11] *1*, wherein said nuclease comprises a recognition domain which specifically binds to said target sequence and a separate catalytic domain which cleaves nucleotide sequences non-specifically and is obtained from a nuclease not comprising said recognition domain.

*33. A method for producing a nuclease in a cell wherein said nuclease, when produced in a cell comprising a target nucleic acid which comprises a target nucleotide sequence specifically binds to said target nucleotide sequence and cleaves said target nucleic acid specifically bound to said nuclease,*

*said method comprising the steps of:*
*a) providing a preparation of a first polynucleotide encoding said nuclease, wherein said preparation does not comprise a second polynucleotide encoding an enzyme which protects said target nucleic acid from said nuclease by specifically binding to said target nucleotide sequence and enzymatically modifying said target nucleic acid such that said target nucleic acid is not cleaved by said nuclease; and*
*b) delivering said preparation of said first polynucleotide encoding said nuclease into said cell by liposomes under conditions such that said first polynucleotide expresses said nuclease, thereby producing said nuclease.*

*34. A method for producing a nuclease in a cell wherein said nuclease, when produced in a cell comprising a target nucleic acid which comprises a target nucleotide sequence specifically binds to said target nucleotide sequence and cleaves said target nucleic acid specifically bound to said nuclease,*

*said method comprising the steps of:*
*a) providing a preparation of a first polynucleotide encoding said nuclease, wherein said preparation does not comprise a second polynucleotide encoding an enzyme which protects said target nucleic acid from said nuclease by specifically binding to said target nucleotide sequence and enzymatically modifying said target nucleic acid such that said target nucleic acid is not cleaved by said nuclease; and*
*b) delivering said preparation of said first polynucleotide encoding said nuclease into said cell under conditions such that said first polynucleotide expresses said nuclease, thereby producing said nuclease;*
*wherein said nuclease is selected from the group consisting of $ZF\text{-}QDR\text{-}F_N$, $ZF\text{-}Sp1C\text{-}F_N$, $ZF\text{-}QNR\text{-}F_N$, $ZF\text{-}QQR\text{-}F_N$ and $ZFHD1\text{-}F_N$.*

*35. A method for producing a nuclease in a cell wherein said nuclease, when produced in a cell comprising a target nucleic acid which comprises a target nucleotide sequence specifically binds to said target nucleotide sequence and cleaves said target nucleic acid specifically bound to said nuclease,*

*said method comprising the steps of:*
*a) providing a preparation of a first polynucleotide encoding said nuclease, wherein said preparation does not comprise a second polynucleotide encoding an enzyme which protects said target nucleic acid from said nuclease by specifically binding to said target nucleotide sequence and enzymatically modifying said target nucleic acid such that said target nucleic acid is not cleaved by said nuclease; and*
*b) delivering said preparation of said first polynucleotide encoding said nuclease into said cell under conditions such that said first polynucleotide expresses said nuclease, thereby producing said nuclease;*
*wherein said target nucleic acid is a DNA:RNA hybrid.*

*36. A method for producing a nuclease in a cell wherein said nuclease, when produced in a cell comprising a target nucleic acid which comprises a target nucleotide sequence specifically binds to said target nucleotide sequence and cleaves said target nucleic acid specifically bound to said nuclease, and wherein said cell in which said nuclease is to be produced is to be cloned, and said cell comprises said target nucleic acid and said target nucleic acid is required for cloning of said cell, said method comprising the steps of:* a) providing a preparation of a first polynucleotide encoding said nuclease, wherein said preparation does not comprise a second polynucleotide encoding an enzyme which protects said target nucleic acid from said nuclease by specifically binding to said target nucleotide sequence and enzymatically modifying said target nucleic acid such that said target nucleic acid is not cleaved by said nuclease; and b) delivering said preparation of said first polynucleotide encoding said nuclease into said cell under conditions such that said first polynucleotide expresses said nuclease, thereby producing said nuclease;

c) providing a third polynucleotide encoding a DNA ligase; and d) delivering said third polynucleotide to said cell before or concurrently with said step of delivering said preparation of said first polynucleotide into said cell, under conditions such that said DNA ligase is produced whereby said target nucleic acid is protected by said DNA ligase from inactivation by said nuclease produced in said cell; and e) cloning said cell producing said nuclease and said ligase.

37. The method of claim 36, wherein said cell is a prokaryotic cell.

38. The method of claim 37, wherein said cell is an E. coli cell.

39. The method of claim 36, wherein said is a eukaryotic cell.

40. The method of claim 39, wherein said cell is a plant cell.

41. The method of claim 39, wherein said cell is a mammalian cell.

42. The method of claim 36, wherein said cell is a mutant or engineered strain that produces an increased level of DNA ligase.

43. The method of claim 36, wherein said nuclease is selected from the group consisting of $ZF\text{-}QDR\text{-}F_N$, $ZF\text{-}SP1C\text{-}F_N$, $ZF\text{-}QNR\text{-}F_N$, $ZF\text{-}QQR\text{-}F_N$ and $ZFHD1\text{-}F_N$.

* * * * *

(12) EX PARTE REEXAMINATION CERTIFICATE (8007th)
United States Patent
Chandrasegaran

(10) Number: US 5,792,640 C2
(45) Certificate Issued: Jan. 25, 2011

(54) GENERAL METHOD TO CLONE HYBRID RESTRICTION ENDONUCLEASES USING LIG GENE

(75) Inventor: Srinivasan Chandrasegaran, Baltimore, MD (US)

(73) Assignee: The National Institutes of Health, Bethesda, MD (US)

Reexamination Request:
No. 90/010,240, Aug. 8, 2008

Reexamination Certificate for:
Patent No.: 5,792,640
Issued: Sep. 9, 2008
Appl. No.: 08/575,361
Filed: Dec. 24, 1995

Reexamination Certificate B1 5,792,640 issued Aug. 11, 1998

Certificate of Correction issued Feb. 9, 1999.

Related U.S. Application Data

(63) Continuation-in-part of application No. 08/346,293, filed on Nov. 23, 1994, now Pat. No. 5,487,994, which is a continuation-in-part of application No. 08/126,564, filed on Sep. 27, 1993, now Pat. No. 5,436,150, which is a continuation-in-part of application No. 08/017,493, filed on Feb. 12, 1993, now abandoned, which is a continuation-in-part of application No. 07/862,831, filed on Apr. 3, 1992, now Pat. No. 5,356,802.

(51) Int. Cl.
*C12Q 1/68* (2006.01)
*C12N 9/22* (2006.01)

(52) U.S. Cl. ........................................ 435/199; 435/91.1
(58) Field of Classification Search ........................ None
See application file for complete search history.

(56) References Cited

U.S. PATENT DOCUMENTS 5,792,640 A * 8/1998 Chandrasegaran .......... 435/199

OTHER PUBLICATIONS

Moure C.M. et al., The crystal structure of the gene targeting homing endonuclease I–ScеI reveals the orgins of its target site specificity, JMB 334:685–695, 2003.*

* cited by examiner

*Primary Examiner*—Sharon Turner

(57) ABSTRACT

The present invention reveals methods for cloning hybrid restriction endonucleases and for enzymatically inactivating a target DNA. The method for cloning hybrid restriction endonucleases involves co-expression of a ligase. A first plasmid contains a gene encoding a DNA ligase. A second plasmid contains a gene encoding a hybrid restriction endonuclease and is compatible with the first plasmid. The method involves transfecting host cells with the first plasmid, so that DNA ligase is produced, followed by transfecting the cells with the second plasmid. The method for enzymatically inactivating a target DNA involves preparing a plasmid, phage, virus or any other delivery vehicle such as a liposome containing a gene encoding a nuclease, delivering the gene into cells, inducing the cells to produce the nuclease and enzymatically inactivating the target DNA.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5-7 and 10-11 were previously cancelled.

Claims 1-4, 8-9, 12-14, 16-21, 23-31, 33 and 36-42 are cancelled.

New claims 44-49 are added and determined to be patentable.

Claims 15, 22, 32, 34-35 and 43 were not reexamined.

*44. A method for producing a non-naturally occurring nuclease in a cell, said method comprising the steps of:*

*a) providing a preparation of a first polynucleotide encoding a non-naturally occurring nuclease comprising a zinc finger domain and a FokI cleavage domain; and*

*b) delivering said preparation of said first polynucleotide encoding said non-naturally occurring nuclease into said cell under conditions such that said first polynucleotide expresses said non-naturally occurring nuclease, thereby producing said non-naturally occurring nuclease.*

*45. The method of claim 44, wherein said polynucleotide encoding said non-naturally occurring nuclease is delivered into said cell by liposomes.*

*46. The method of claim 44, wherein said polynucleotide encoding said non-naturally occurring nuclease further comprises control elements.*

*47. The method of claim 44, wherein said cell is selected from the group consisting of a prokaryotic cell and a eukaryotic cell.*

*48. The method of claim 47, wherein said cell is a plant cell.*

*49. The method of claim 47, wherein said cell is a mammalian cell.*

* * * * *